United States Patent [19]
Fuse et al.

[11] Patent Number: 6,104,493
[45] Date of Patent: Aug. 15, 2000

[54] METHOD AND APPARATUS FOR VISUAL INSPECTION OF BUMP ARRAY

[75] Inventors: Takashi Fuse; Youji Nishiyama; Yoshitaka Oshima; Fumiyuki Takahashi; Hiroyuki Tsukahara, all of Kawasaki, Japan

[73] Assignee: Fujitsu Limited, Kawasaki, Japan

[21] Appl. No.: 09/310,089

[22] Filed: May 12, 1999

[30] Foreign Application Priority Data

May 14, 1998 [JP] Japan ................................ 10-131955
May 21, 1998 [JP] Japan ................................ 10-139682

[51] Int. Cl.[7] ............................................... F01B 11/28
[52] U.S. Cl. ......................... 356/379; 356/372; 356/380; 356/376
[58] Field of Search ................................ 356/372, 380, 356/379, 376

[56] References Cited

U.S. PATENT DOCUMENTS 5,159,643  10/1992  Kaga et al. ............................... 382/8
5,307,292   4/1994  Brown et al. .......................... 364/564

Primary Examiner—Frank G. Font
Assistant Examiner—Reginald A. Ratliff
Attorney, Agent, or Firm—Armstrong, Westerman, Hattori, McLeland & Naughton

[57] ABSTRACT

The bump height is measure din a sample area on a wafer, the bump height distribution on the wafer is estimated on the bases of the measured value, the portion where the estimated height distribution is out of a predetermined range is determined as an inspection area, and the bump height is measured in the inspection area, and a chip area having a bump height out of a predetermined range is judged to be defective. Data of the inspection areas and inspection results are accumulated, and the inspection density is renewed on the basis of the accumulated data. In another method, the inspection area is divided into rectangular blocks so that each block has a width of approximately equal to a light beam scanning length and a distance between any adjacent bumps in the feeding direction is less than a predetermined value, feeding path being perpendicular to the scanning direction. Block feed time and between-block feed time are calculated, a whole feeding path whose total feed time of the block and between-block feed time are minimum is found, and bump height is measured with receiving reflected light from the bump while feeding along the found feeding path.

25 Claims, 37 Drawing Sheets

FIG.10
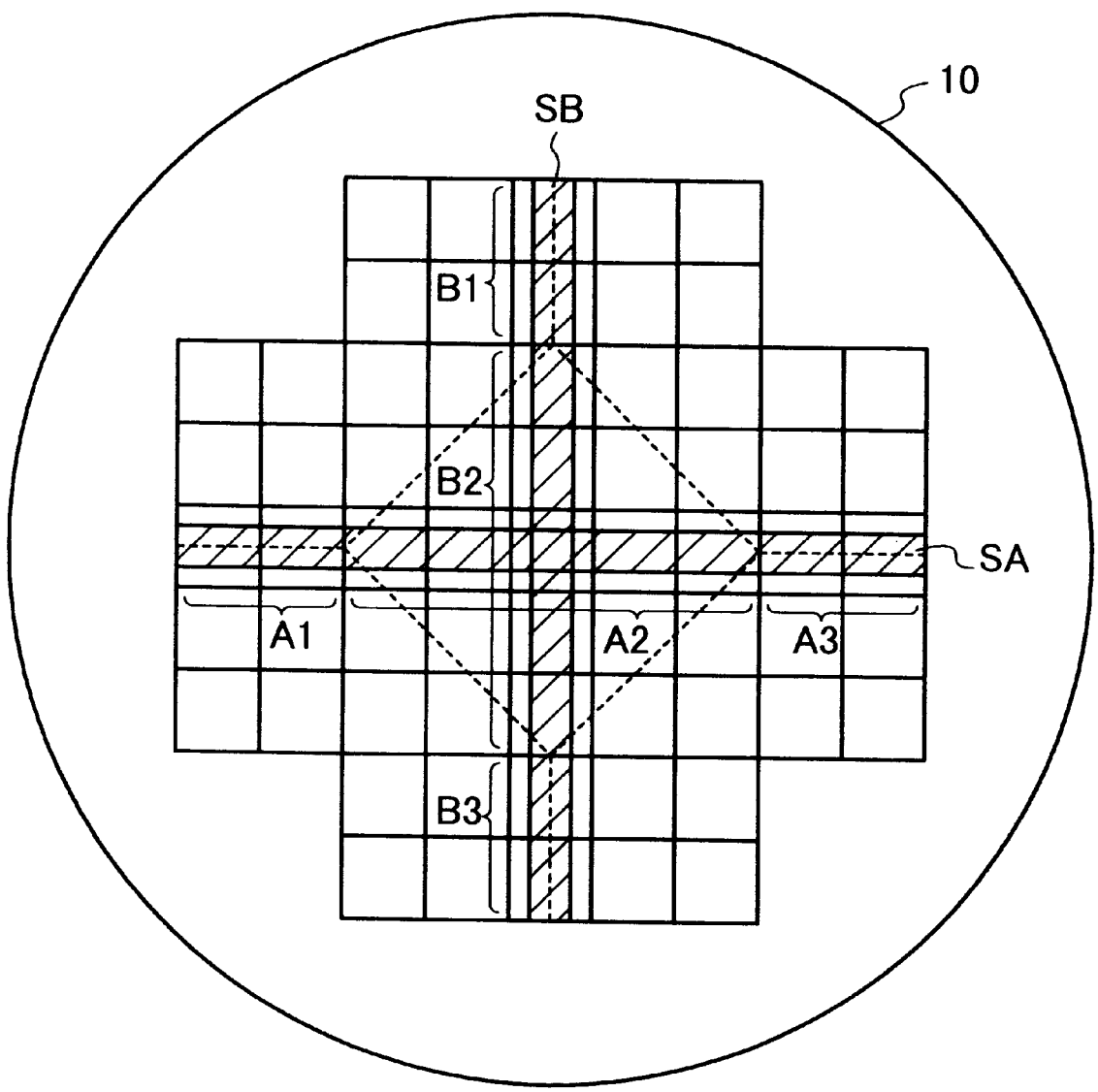
---------- SECTIONING LINE OF HEIGHT ESTIMATION AREA
 SAMPLE AREA

FIG.12
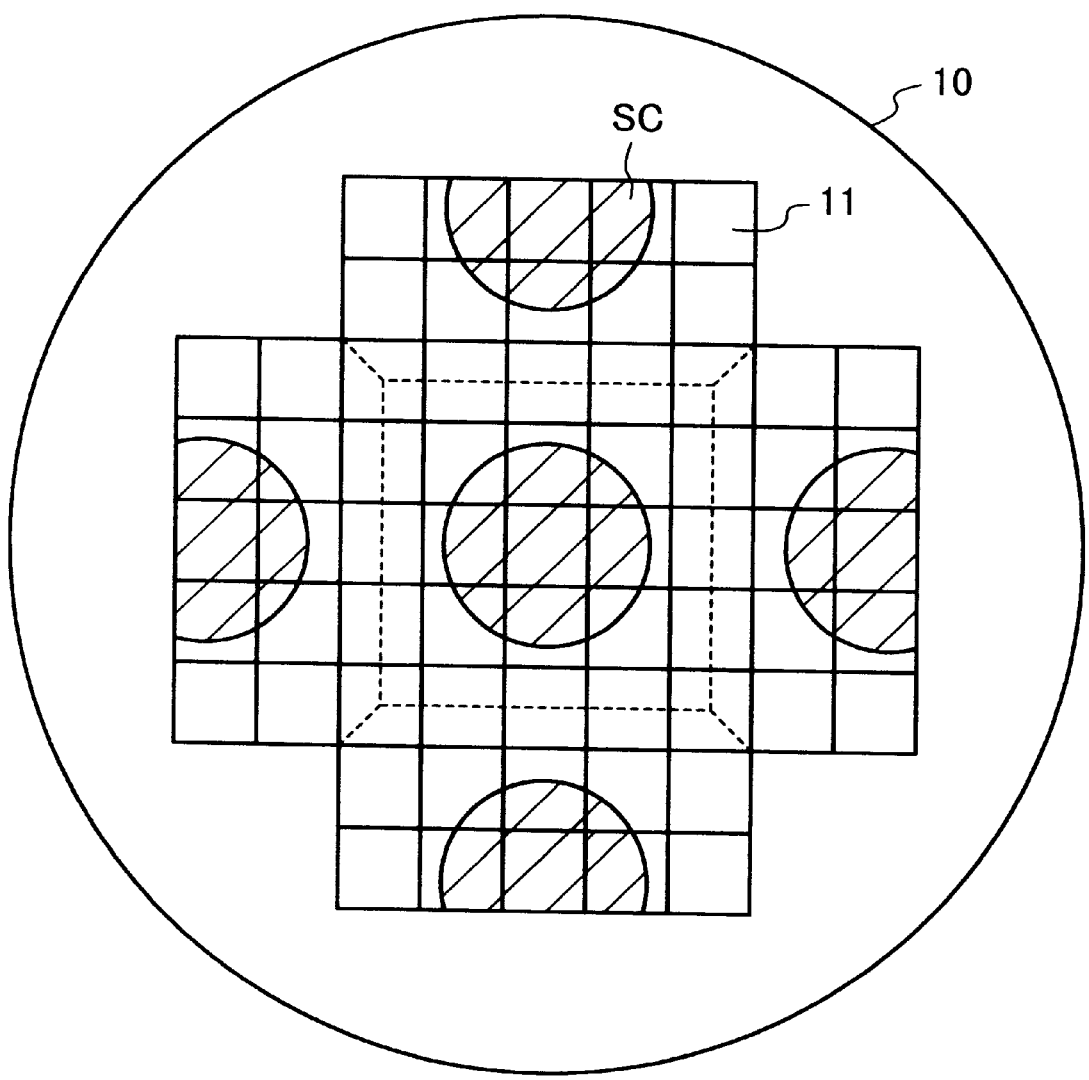
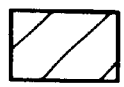 SECTIONING LINE OF HEIGHT ESTIMATION AREA
SAMPLE AREA

FIG.13
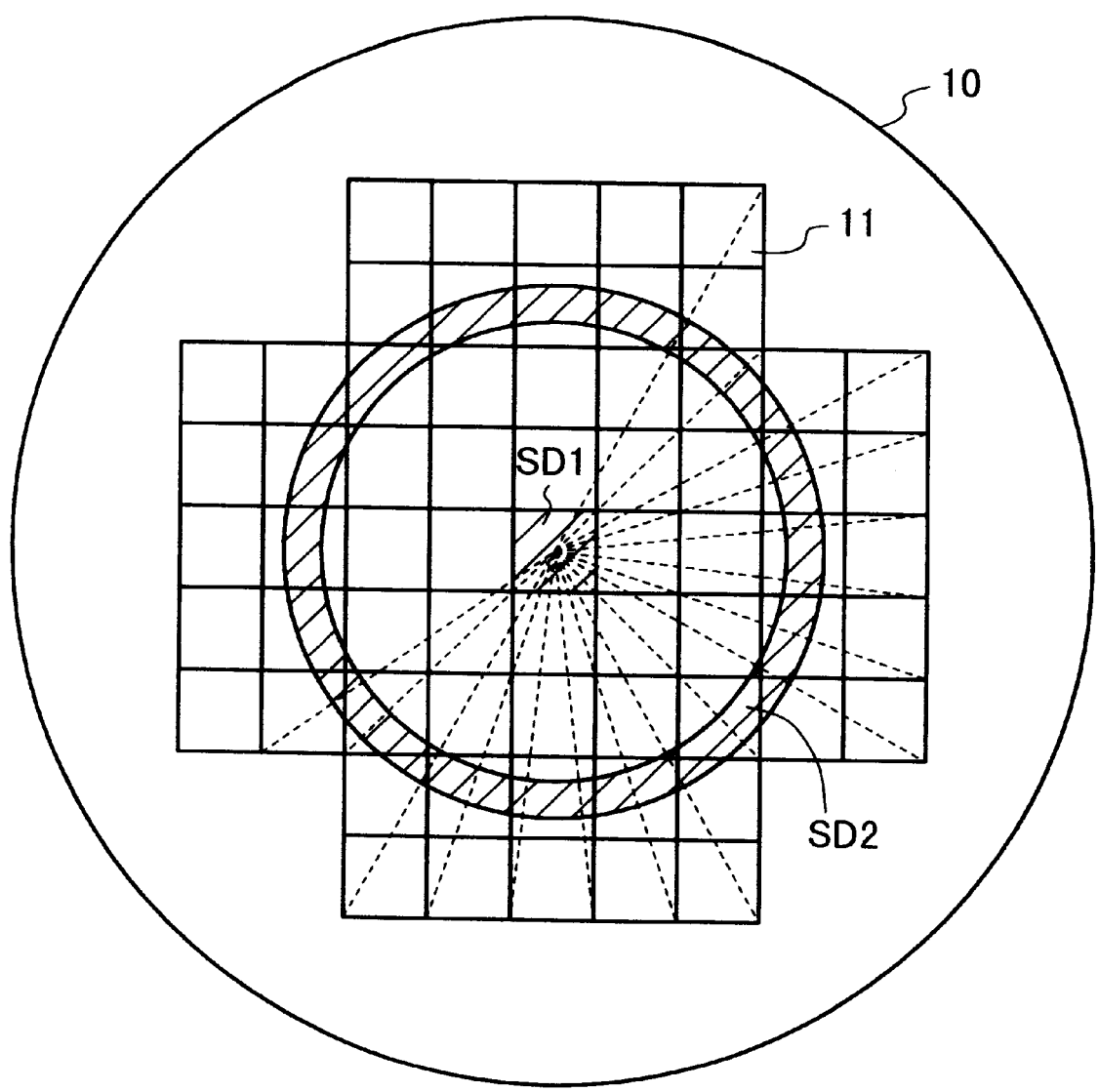
 SAMPLE AREA

----------- FIRST BOUNDARY LINE OF INSPECTION AREA

—-—-—- EXPANDED BOUNDARY LINE OF INSPECTION AREA

FIG.16
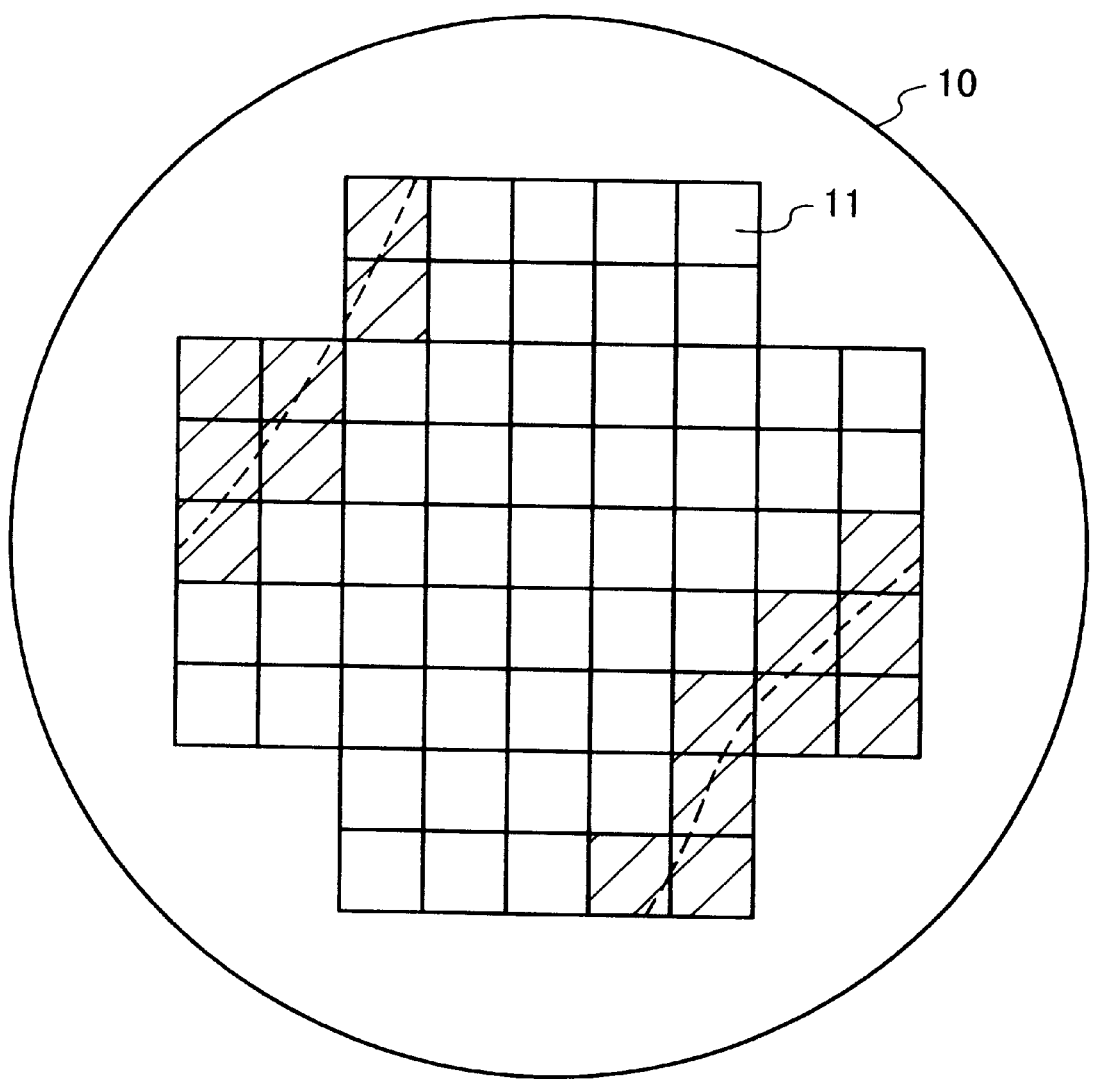
·········· FIRST BOUNDARY LINE OF INSPECTION AREA
 EXPANDED INSPECTION AREA

FIG.17
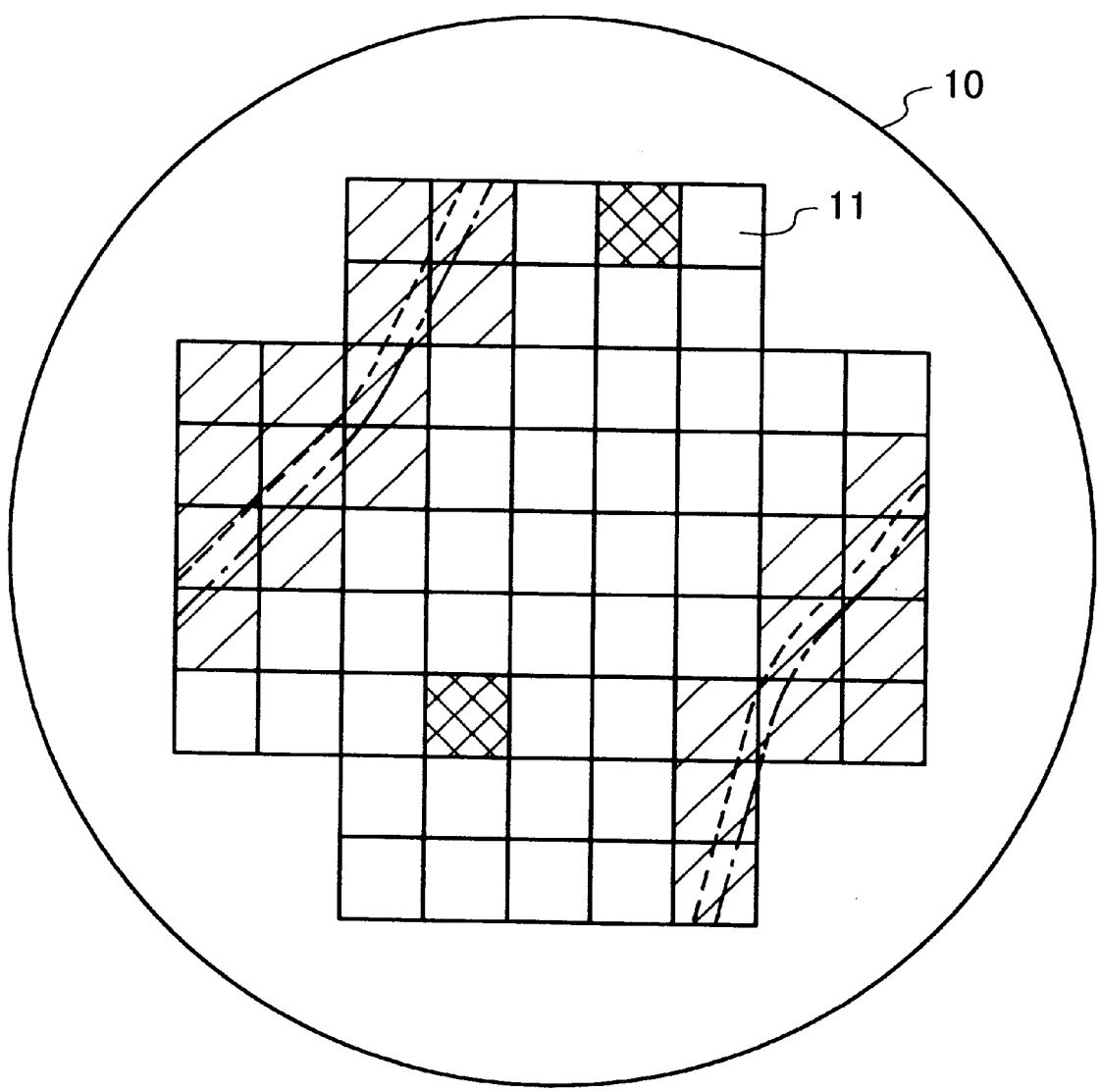
 EXPANDED INSPECTION AREA
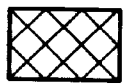 SAMPLING INSPECTION AREA

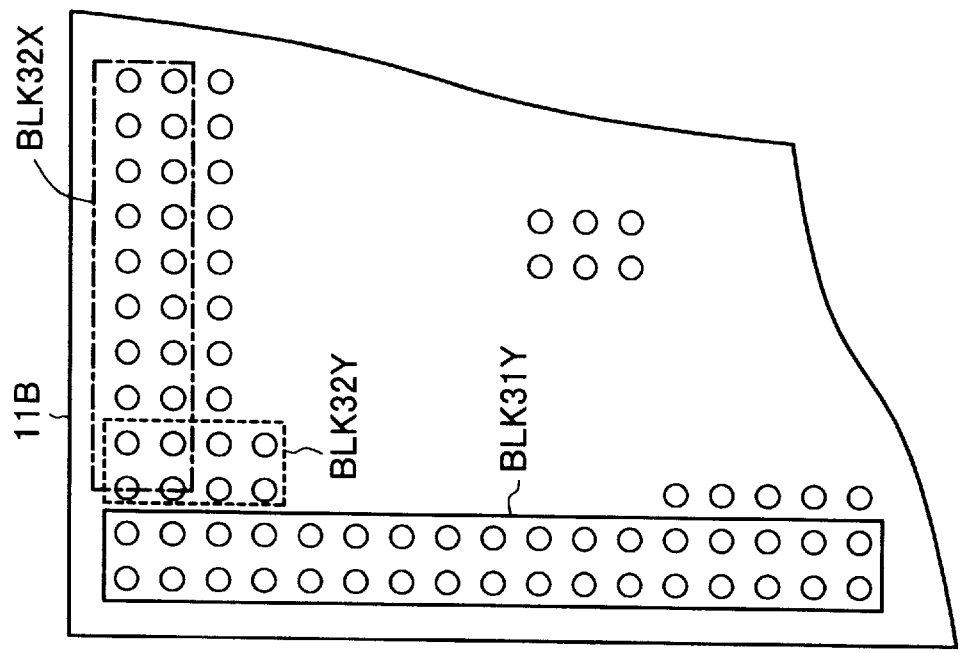
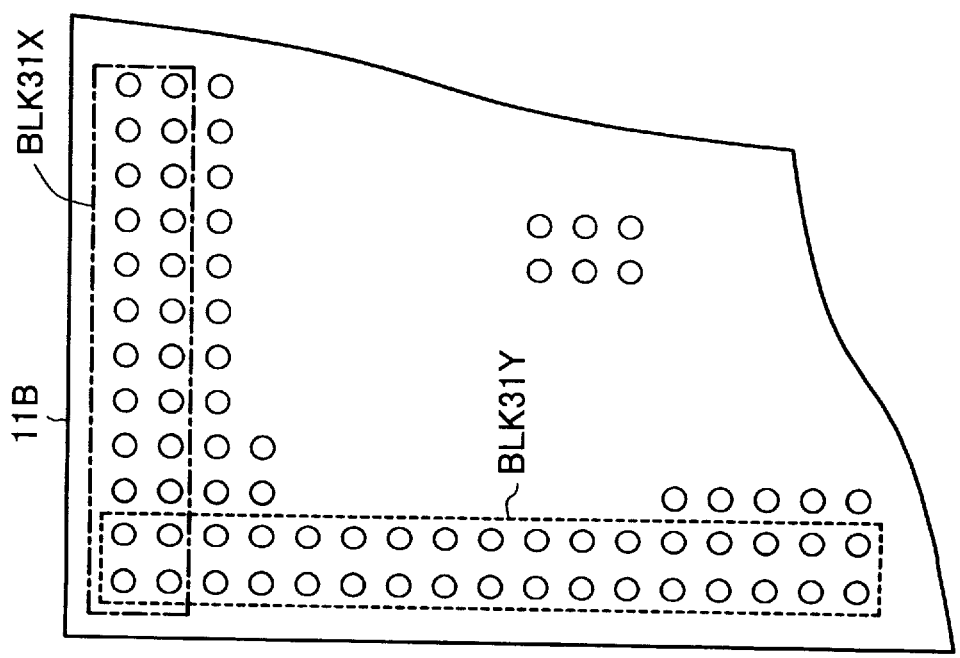

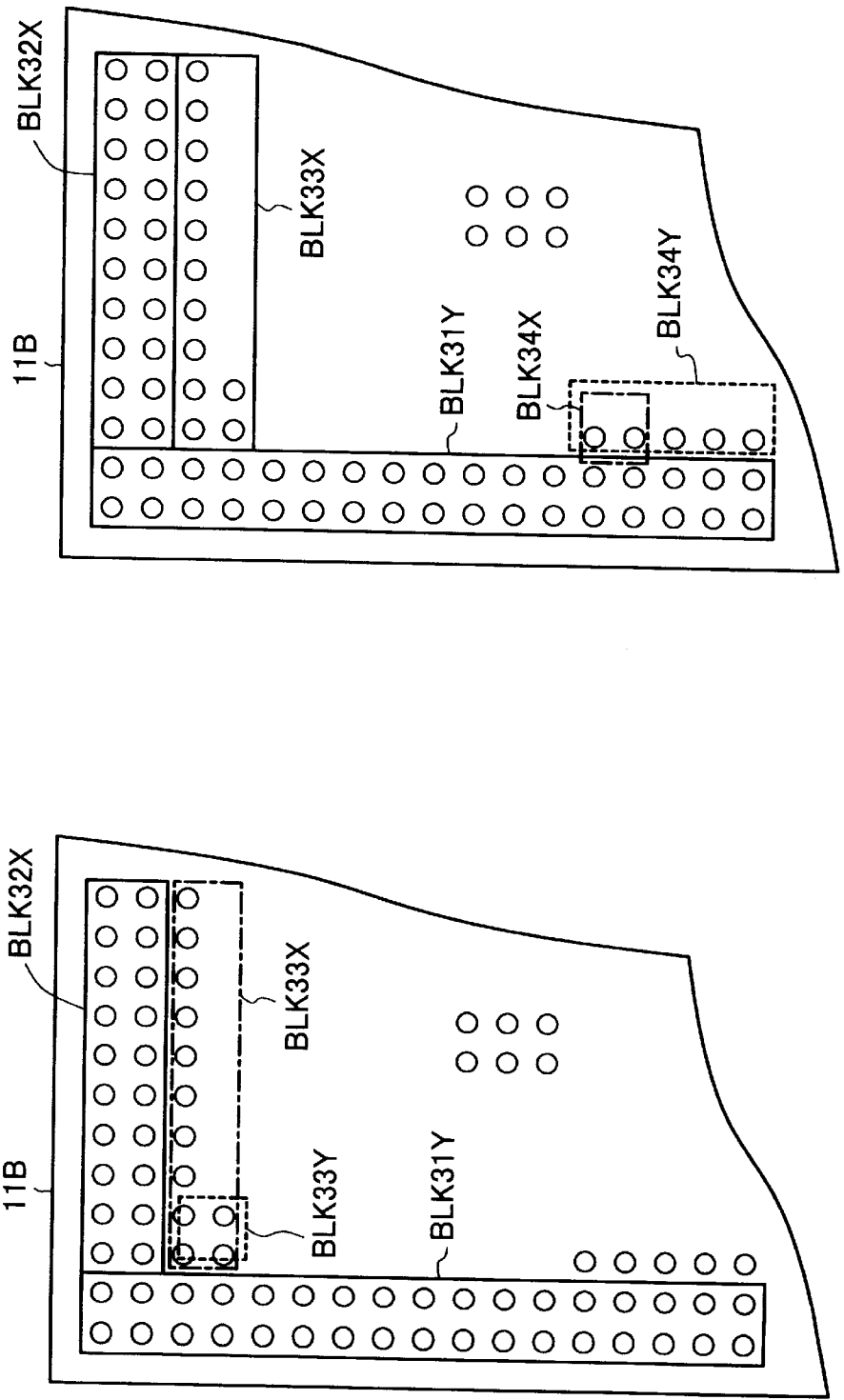

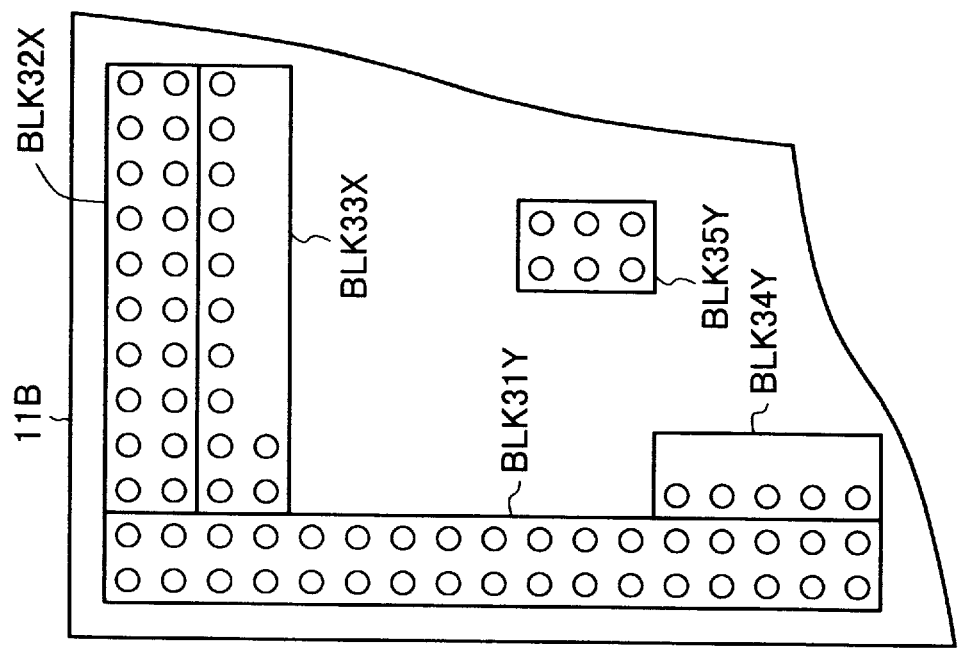
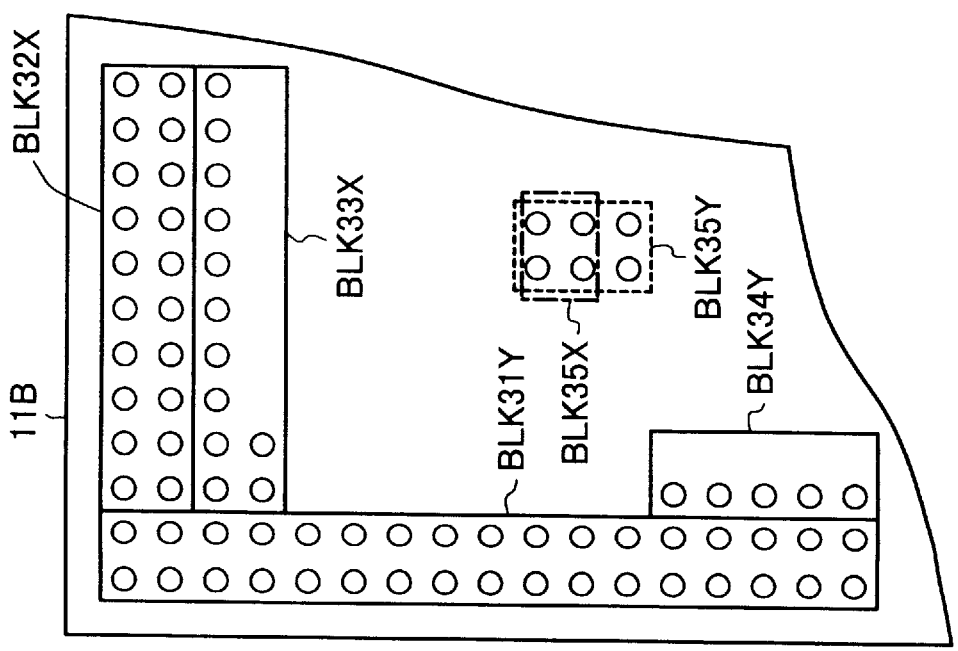

METHOD AND APPARATUS FOR VISUAL INSPECTION OF BUMP ARRAY

BACKGROUND OF THE INVENTION

1. Field of the Invention

The present invention relates to a method and an apparatus for visual inspection of a bump array formed on a base material such as a flip chip.

2. Description of the Related Art

Regarding a flip chip on which a bump array is formed, a high-density mounting is enabled by bonding the tops of the bumps onto a substrate. If there exists differences in the height of the bumps, insufficient connection and/or non-connection may occur after the bumps are bonded to a substrate, and if the diameter of a bump is excessively large, a short-circuiting with an adjacent bump may occur. Although these defectiveness can be detected by an electric test after mounting the flip chip onto a substrate, it is preferable that they are detected by a visual inspection before mounting a flip chip.

Therefore, a visual inspection apparatus is used in order to judge the quality of bumps by measuring one or more of the height, diameter or volume of bumps on the basis of triangulation, etc., with irradiating a laser beam to an object to be inspected and receiving the reflected light with a sensor.

However, since thousands of bumps are arranged on a chip, the time for a visual inspection of bumps is relatively longer. In particular, as shown in FIGS. 37(A) and 37(B), in a case where a visual inspection is carried out with respect to bumps 12 which are arrayed and bonded onto the respective chip areas 11 before dividing the wafer into chips with a number of chip areas 11 formed on a wafer 10, a higher speed inspection is required.

Further, although the array figure of bumps differs according to the kinds of chips, in the prior art, an object to be inspected is fed in zigzag regardless of the bump array figure. This results in a longer feed time.

SUMMARY OF THE INVENTION

Accordingly, it is an object of the present invention to provide a method and an apparatus for visual inspection of bumps which enable a higher speed inspection with increasing the efficiency of inspection.

In the present invention, there is provided a method measuring a geometrical quantity of the bumps, comprising the steps of: (a) determining a sample area having part of bumps in the sample area; (c) estimating a geometrical quantity distribution of the bumps on the substrated based on the measured value at the step (b); (d) determining an inspection area based on the geometrical quantity distribution; and (e) measuring the geometrical quantity of the bumps in the inspection area instead of all the bumps on the substrate.

With the present invention, the geometrical quantity of the bumps in the sample area is measured to limit the inspection area in which defective bump may exist, and the inspection of bumps is carried out only for the inspection area. Therefore, a high-speed inspection of high efficiency can be achieved.

BRIEF DESCRIPTION OF THE DRAWINGS

FIG. 10 is a view showing separation of sample area and sectioning lines of height estimation areas in the second embodiment according to the present invention;

FIG. 12 is a view showing sample areas and separated height estimation areas in the third embodiment according to the present invention;

FIG. 13 is an illustration of sample areas and height estimation planes in the fourth embodiment according to the present invention;

FIG. 16 is an illustration of enlargement of an inspection area in the sixth embodiment according to the present invention;

FIG. 17 is an illustration of enlargement of an inspection area in the seventh embodiment according to the present invention;

FIGS. 20(A) and 20(B) are illustrations of the brightness distribution of reflected light in the tenth embodiment according to the present invention, wherein FIG. 20(A) is an illustration of laser beam scanning for a bump, and FIG. 20(B) is an illustration of the binary brightness distribution of reflected light in the case of FIG. 20(A);

FIGS. 34(A) and 34(B) are illustrations of the first and second loop processes in FIG. 32, respectively;

FIGS. 35(A) and 35(B) are illustrations of the third and fourth loop processes in FIG. 32, respectively;

FIGS. 36(A) and 36(B) are illustrations of the fifth loop process in FIG. 32.

DESCRIPTION OF THE PREFERRED EMBODIMENTS

Figure 1:
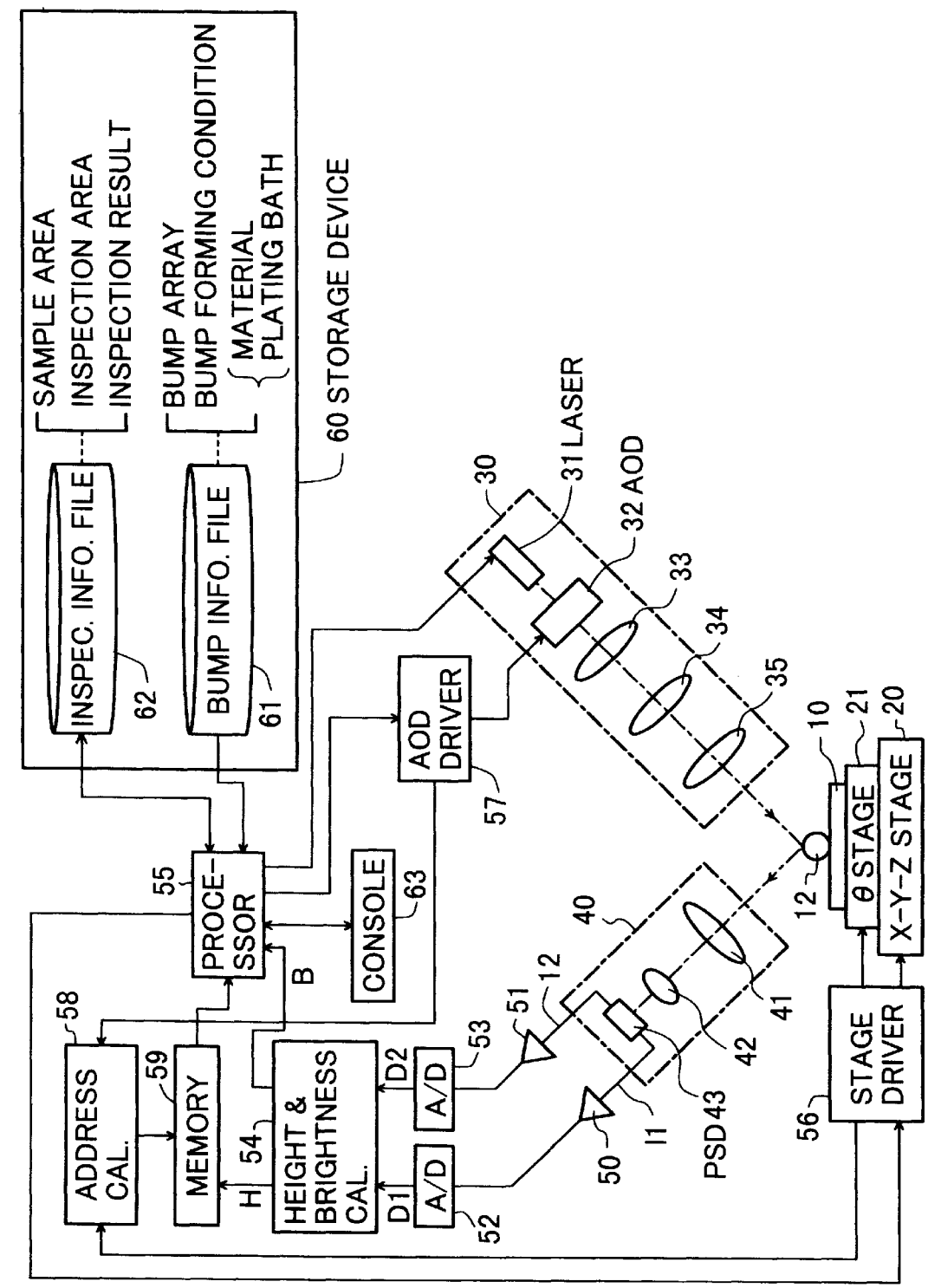
FIG. 1 is a schematic diagram showing an apparatus for visual inspection of bumps of the first embodiment according to the present invention.

Referring now to the drawings, wherein like reference characters designate like or corresponding parts throughout several views, preferred embodiments of the present invention are described below.

First Embodiment

FIG. 1 shows a schematic configuration of an apparatus for visual inspection of bumps.

A wafer 10 which is an object to be inspected is mounted onto an X-Y-Z stage 20 via a θ stage 21. A number of chip areas are formed on the wafer 10, and bumps 12 are arrayed and formed on each chip area. A light beam scanner 30 and a height detector 40 are arranged on the wafer 10, which are fixed in use.

Figure 2:
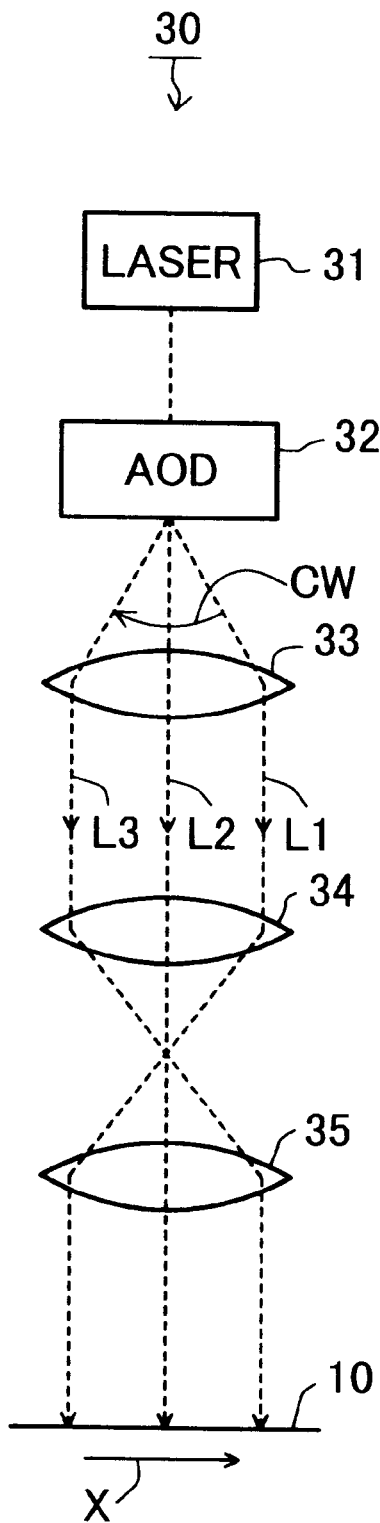
FIG. 2 is an illustration of the optical path of the light beam scanner in FIG. 1.

In the light beam scanner 30, a light beam emitted from a laser 31 is scanned in the perpendicular direction to the drawing paper by an AOD (acousto-optic deflector) 32, passes through relay lenses 33 and 34 and an objective 35, and is second on the wafer 10 in the perpendicular direction to the drawing paper. That is, as shown in FIG. 2, the laser beam is scanned in the CW direction by the AOD 32 and changes from an optical path L1 through an optical path L2 to an optical path L3, whereby the light spot scans on the surface of the wafer 10 in an X direction as illustrated.

In the height detected 40, the light beam reflected on the wafer 10 passes through the objective 41 and image-forming lens 42 and is imaged on the light receiving plane of a PSD (position sensitive detector) 43.

Currents I1 and I2 outputted from one and the other ends of the PSD 43 are converted to voltage and amplified by amplifiers 50 and 51, respectively. The outputs of the amplifiers 50 and 51 are digitized to D1 and D2 by A/D converters 52 and 53, respectively, and are provided in a height and brightness calculation circuit 54. The circuit 54 calculates the brightness B=(D1+D2) and normalized height H=(D1−D2)/(D1+D2) of a light spot on the wafer 10.

Figure 3:
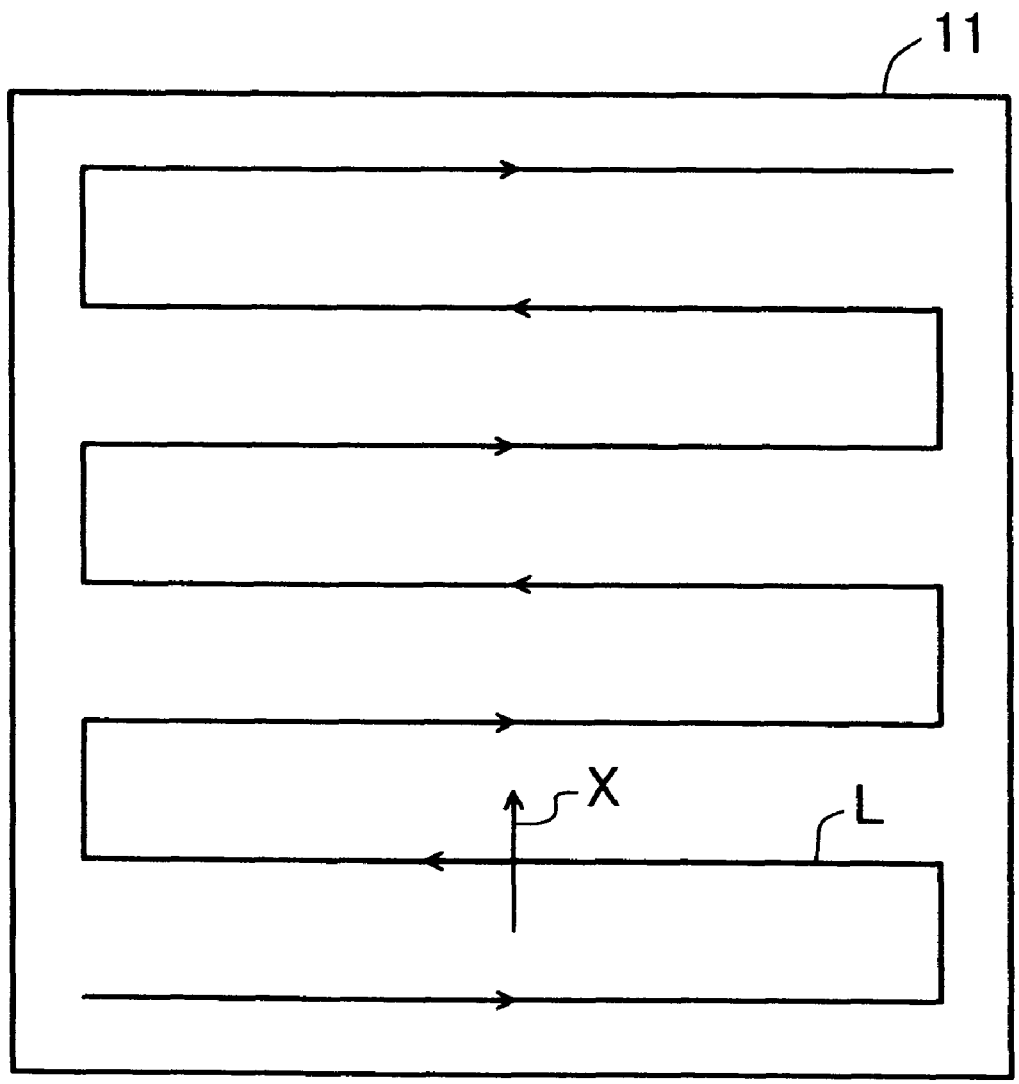
FIG. 3 is an illustration showing a locus of feed by an X-Y-Z stage, and a scanning direction by an acousto-optic deflector.

Meanwhile, a processing unit 55 drives an X-Y-Z stage 20 via a stage drive circuit 56 so that the locus of the light spot formed on the wafer 10 by the light beam scanner 30 whose AOD 32 is not operating becomes line L in FIG. 3. The processing unit 55 drives the AOD 32 via an AOD drive circuit 57. When the AOD 32 is driven, the scanning direction of the light spot is the X direction which is perpendicular to the feed locus L. The feed position of the X-Y-Z stage 20 and the information regarding light spot position included in the output signal of the AOD drive circuit 57 is provided from the stage drive circuit 56 and AOD drive circuit 57 to an address calculation circuit 58 which calculates a memory address of height H on the basis thereof, whereby a memory 59 is addressed. The height H coming from the height and brightness calculation circuit 54 is written at this address.

The processing unit 55 controls an optical output of the laser 31 in a given range so that the brightness B coming from the height and brightness calculation circuit 54 becomes a predetermined value. If the brightness B is lower than a given value because the intensity of the incident light into the height detector 40 is weak, the memory 59 is made disable.

The memory 59 is divided into, for example, storage areas MA and MB (not shown), wherein the height H is transferred with direct memory access (DMA) into one of the area MA or MB, and data in the other area is processed by the processing unit 55 is parallel thereto, and the areas MA and MB are changed over alternately.

In a storage device 60, a bump information file 61 and an inspection information file 62 are stored. The bump information file 61 includes bump array information extracted from CAD data and bump forming information such as bump materials and plating bath numbers which are used when bumps are plated. The processing unit 55 reads bump array information from the bump information file 61 and drives the stage drive circuit 56 and AOD drive circuit 57 on the basis thereof.

A console 63 consisting of an input device such as a keyboard or a mouse, and a display device, is connected to the processing unit 55.

Figure 4A:
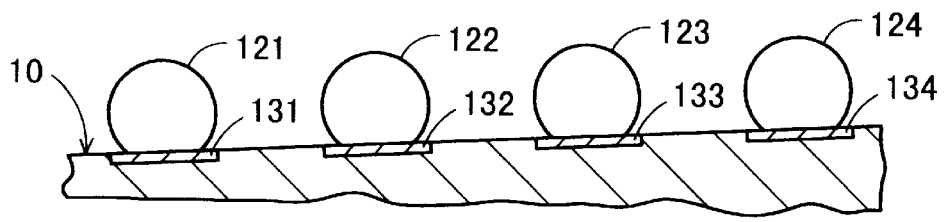
FIGS. 4(A) through 4(C) are illustrations of a method of measuring bump height.
Figure 4B:
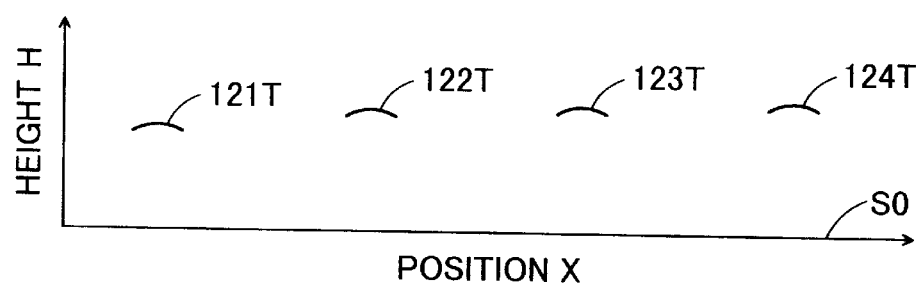
Figure 4C:
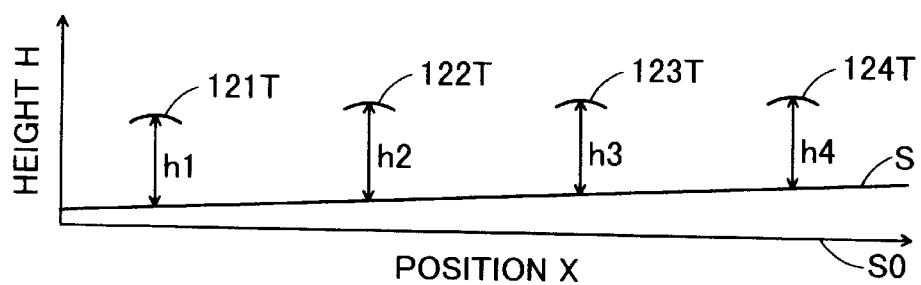

In FIG. 4(A), bumps 121 through 124 are bonded on pads 131 through 134, respectively, formed on the wafer 10. The bumps 121 through 124 are scanned with light beam by the AOD 32, and the height H is stored in the memory 59, whereby, the distribution of heights H as shown in FIG. 4(B) are obtained in the memory 59. 121T through 124T show the height of the top portions of the bumps 121 through 124, respectively. Before the scanning with light, height of marks, pads or wiring (not shown) formed at three or more points on the wafer 10 are measured in the same way as above, whereby the surface S of the wafer 10 is determined as shown in FIG. 4(C). The heights h1 through h4 of the top of the portions 121T through 124T from the surface S are obtained by the processing unit 55.

Figure 5:
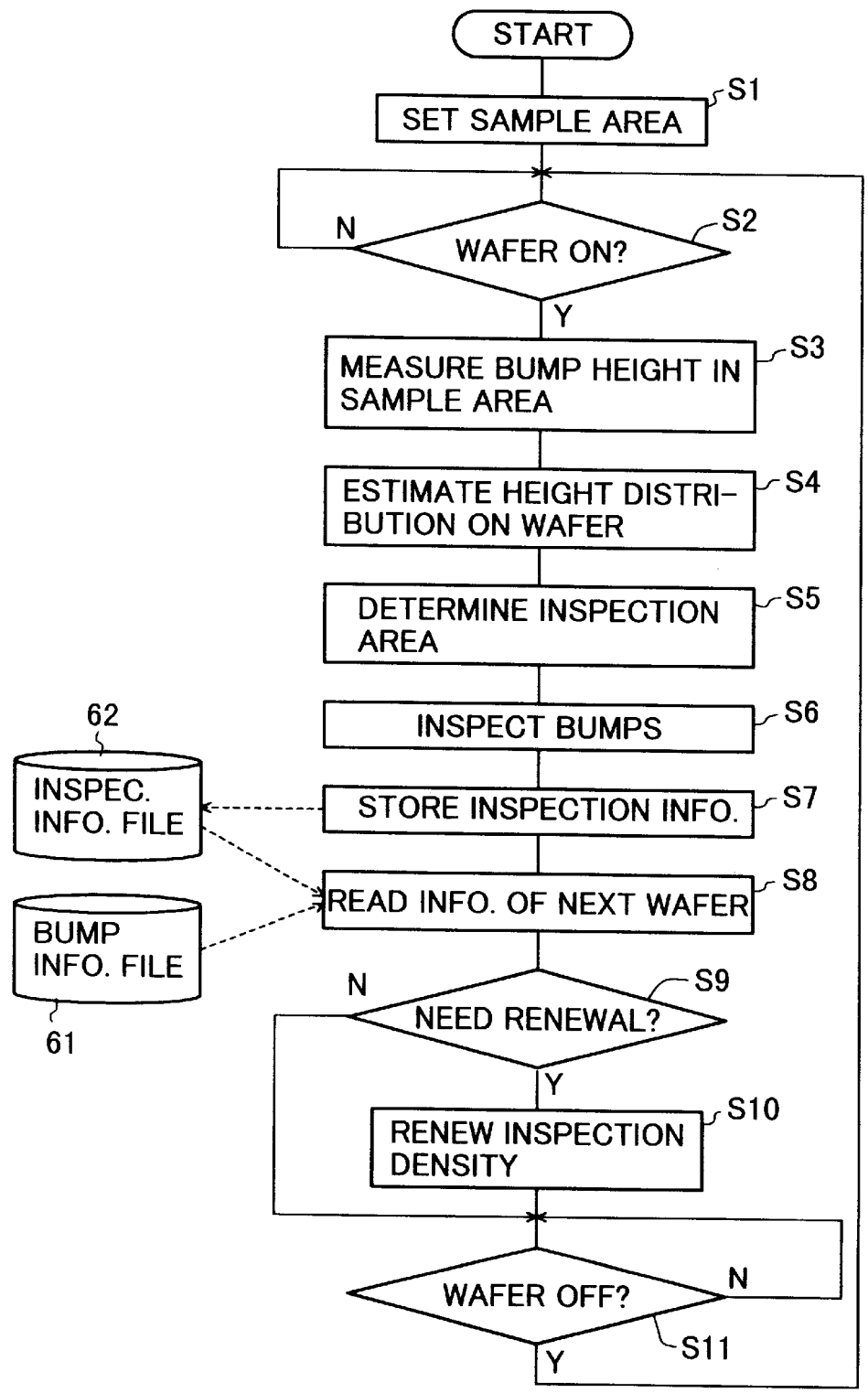
FIG. 5 is a general flowchart showing a procedure of visual inspection of bumps.

Next, referring to FIG. 5, a description is given of the inspection procedure performed by the processing unit 55. Hereinafter, reference characters in parenthesis denote step identification in the drawings.

Figure 6:
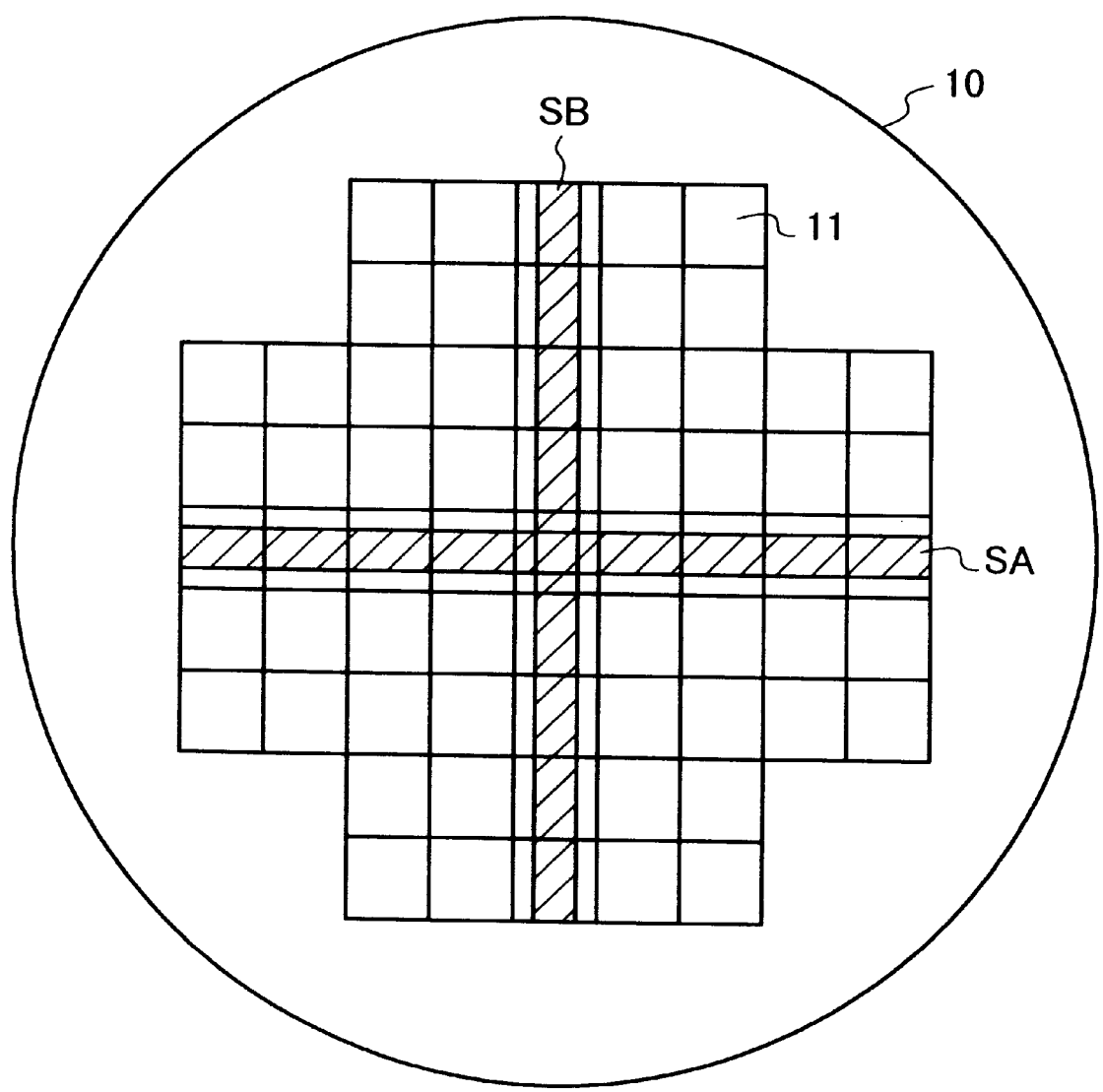
FIG. 6 is a view showing a sample area on a wafer.

(S1) A wafer 10 being an object to be inspected, as shown in FIG. 6, on which a number of chip areas 11 are formed, are displayed on the display of the console 63. An operator determines sample areas on the wafer 10 with operating an input device of the console 63. Band-figure sample areas SA and SB crossed and hatched are shown in FIG. 6.

(S2) Waiting until it is detected that the wafer 10 is transferred by a transfer equipment (not shown) and is mounted on the θ stage 21, the process proceeds to a step S3.

(S3) The height of the bumps is measured as described above with feeding and scanning the sample areas by the X-Y-Z stage 20 and AOD 32, respectively.

Figure 7:
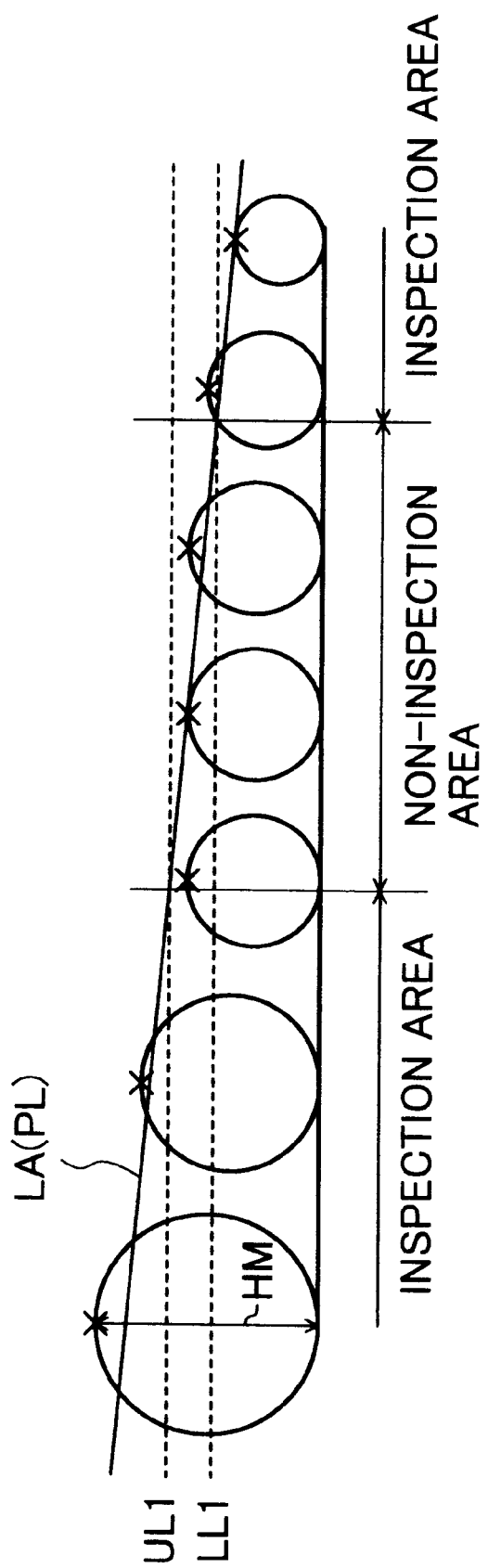
FIG. 7 is an illustration of an approximate line of bump height and a method of judging inspection areas.

(S4) From the measurement results, the height distribution of all the bumps on the wafer 10 is estimated. That is, the mean value HM of the bump heights in each local area in the sample area SA, for example, in each of the chip areas, is obtained, and the mean values HM are approximately by a straight line LA, as shown in FIG. 7, determined with the least square approximation method. Cross marks 'X' in FIG. 7 denote the mean values HM, and circles denote bumps with height of the mean values HM. Another approximate line regarding the sample area SB in FIG. 6 is obtained in the same way as above. The height distribution of all the bumps on the wafer 10 is estimated with a plane PL on which the both straight lines exist.

Figure 8:
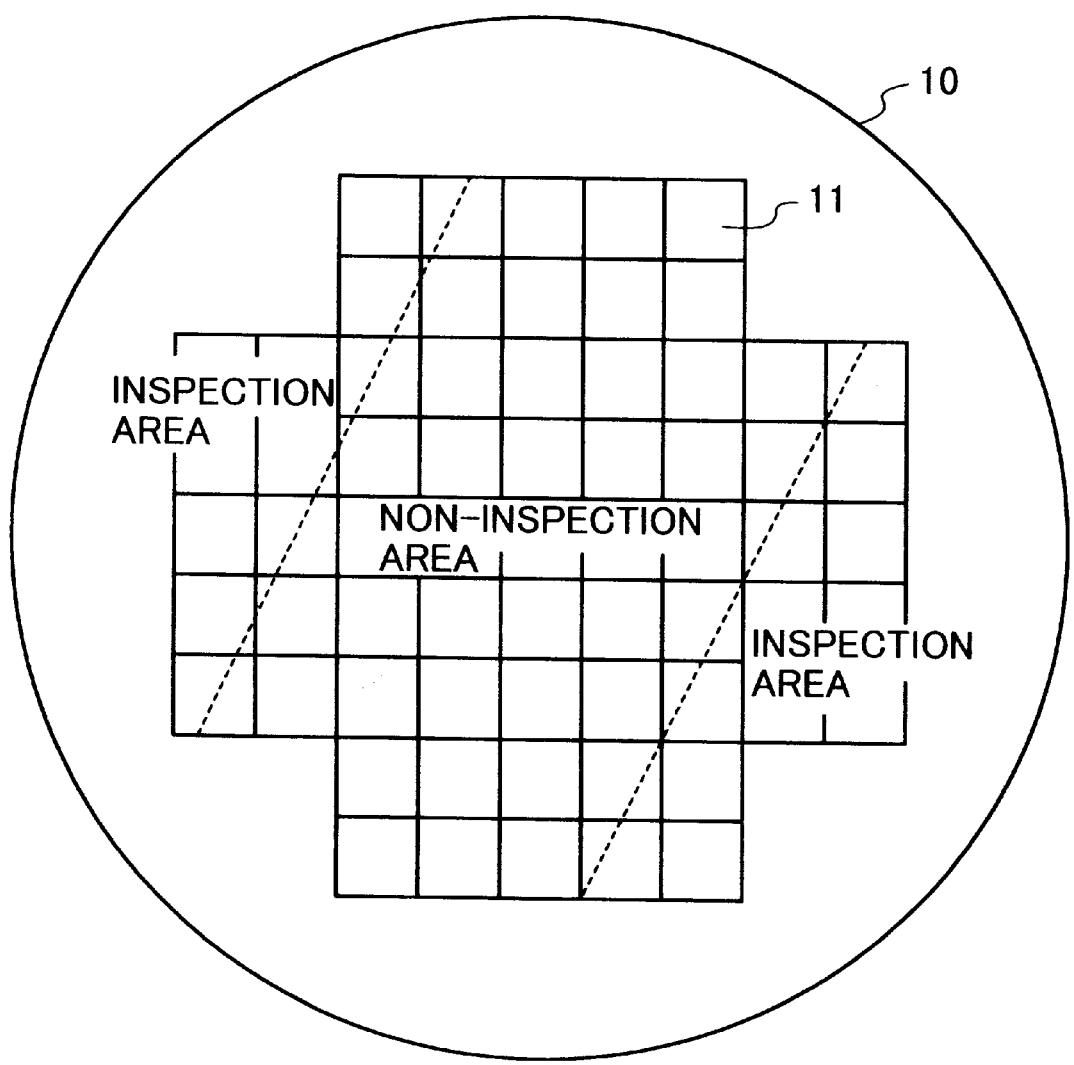
FIG. 8 is a view showing inspection areas on a wafer.

(S5) As shown in FIG. 7, the areas where the approximate plane PL is higher than the predetermined upper limit value UL1 and is lower than the predetermined lower limit value LL1 are determined as inspection areas. These inspection areas are, for example, ones partitioned by dotted lines in FIG. 8.

The upper limit value UL1 and lower limit value LL1 are determined so that the ratio of the number of defectives in inspection areas on a wafer to the number of defectives on the wafer becomes almost equal to 1 and the inspection areas become as narrow as possible.

(S6) The bump height is measured with scanning and feeding only the inspection areas, and even if one of the bumps whose height H is outside a predetermined range is found in a chip area, the chip area is judged as a defective.

(S7) The data of the sample areas, inspection areas and results of inspections are stored as inspection information in the inspection information file 62.

Inspection information is accumulated in the inspection information file 62, and for this, statistical analyses are carried out in order to increase the reliability and efficiency of inspection. For example, in a case where plating is performed on bumps, the number of the used plating bath is stored in the inspection information file 62, and as shown in FIG. 9, the mean value of the defective ratio in inspection areas is obtained for every plating bath number.

(S8) With respect to the wafer 10 of the next object to be inspected, information including a plating bath number is read from the bump information file 61, and it is judged whether or not the inspection density is renewed, with reference to information accumulated in the inspection information file 62. Herein, the inspection density means a ratio of the inspection areas to all the chip areas on a wafer 10 or a ratio of inspection areas in a local bump areas to the local bump areas.

Figure 9:
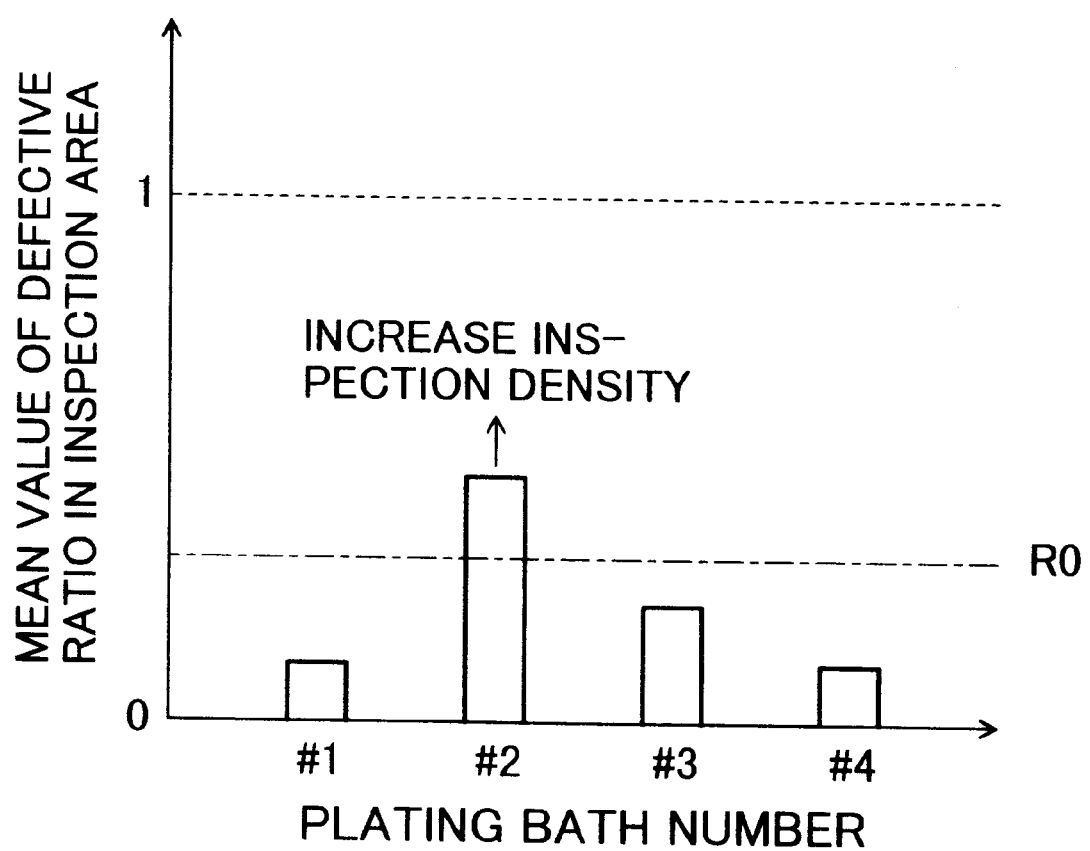
FIG. 9 is a bar graph showing the mean value of defective ratio in inspection area for each plating bath.

For example, in FIG. 9, if the mean value of the defective ratio having the corresponding plating bath number exceeds a set value R0, or if the ratio of the number of defective chips on the boundary lines of an inspection area to the number of chips in the inspection area exceeds a set value, it is judged that renewal is necessary.

(S9) If it is judged that the renewal is necessary, then the process proceeds to a step S11.

(S10) The inspection density is renewed in order to make an inspection area more proper. For example, in FIG. 9, if the means value of the defective ratio exceeds the set value R0, the inspection density is increased by making the range, in FIG. 7, between the upper limit value VL1 and the lower limit value LL1 narrow.

(S11) The process proceeds to the step S2 after waiting for a wafer getting off from the θ stage 21.

According to the first embodiment, since areas which are considered to include defectives are determined as inspection areas, and the bump heights are measured for only the inspection areas to judge whether or not chip area is defective, it is possible to carry out a high speed inspection at high efficiency. Further, since inspection areas that are more proper can be determined by utilizing information accumulated in the inspection information file 62, the reliability of inspection will be secured.

Second Embodiment

Figure 11:
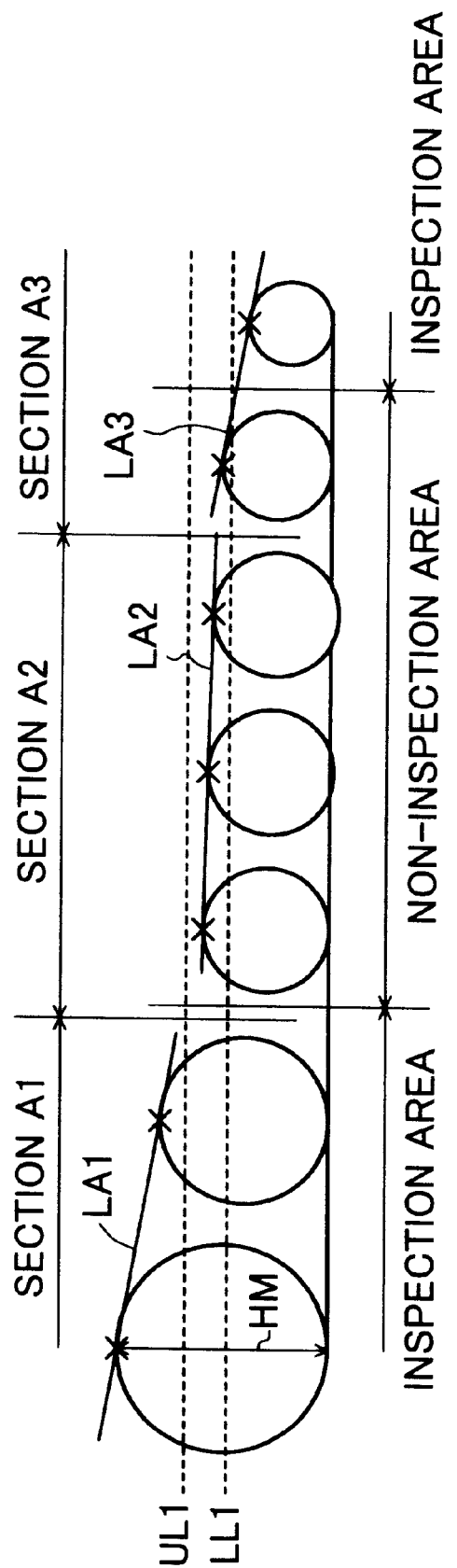
FIG. 11 is an illustration of an approximate line of bump height and a method of judging inspection areas in the second embodiment according to the present invention.

In the second embodiment according to the present invention, as shown in FIG. 10, the sample area SA is divided into sections A1, A2, and A3, and the bump height of the respective areas is approximated by straight lines LA1, LA2 and LA3 as shown in FIG. 11. In the same way, the sample area SB is divided into sections B1, B2 and B3, and the bump height is approximated for each of the areas. Then, the bump height of the respective areas section by dotted lines in FIG. 10 is approximated by surfaces on which these straight lines pass.

All the other points of the second embodiment are the same as those of the first embodiment.

According to the second embodiment, since it is possible to estimate the bump height distribution more accurately than in the case of the first embodiment, the reliability of inspection will improve.

Third Embodiment

FIG. 12 shows a way of taking sample areas SC of the third embodiment according to the present invention.

The area of the wafer 10 are sectioned by dotted lines, and the sample areas SC are determined in the respective areas, wherein the height of each sectioned area is estimated on the basic of that of the sample area SC.

All the other points thereof are the same as those of the above-described first embodiment.

Fourth Embodiment

FIG. 13 shows a way of taking sample areas of the fourth embodiment according to the present invention.

Figure 14:
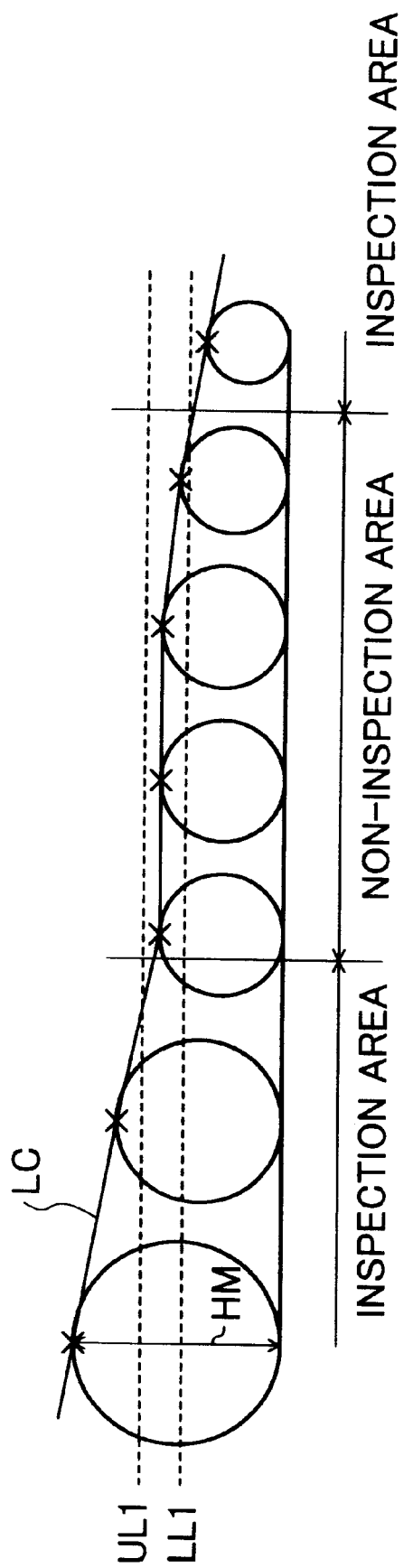
FIG. 14 is a view showing an approximate curve of the height of bumps in a ring-shaped sample area in FIG. 13.

A sample area SD1 of the middle portion on the wafer 10 and a ring-shaped sample area SD2 around the area SD1 are determined. The bump height in the sample area SD2 is approximated by a curved line or a polygonal line LC, as shown in FIG. 14, passing each average bump height HM of local area, for example, chip area. The average bump height of the sample area SD1 is regarded as the height of the center of the sample area SD1. The bump height on the wafer 10 is estimated as a surface obtained by turning a straight line which starts from this center point and passes a point on the approximate line LC. The dotted lines in FIG. 13 show part of these straight lines.

All the other points of the fourth embodiment are the same as those of the first embodiment.

Fifth Embodiment

Figure 15:
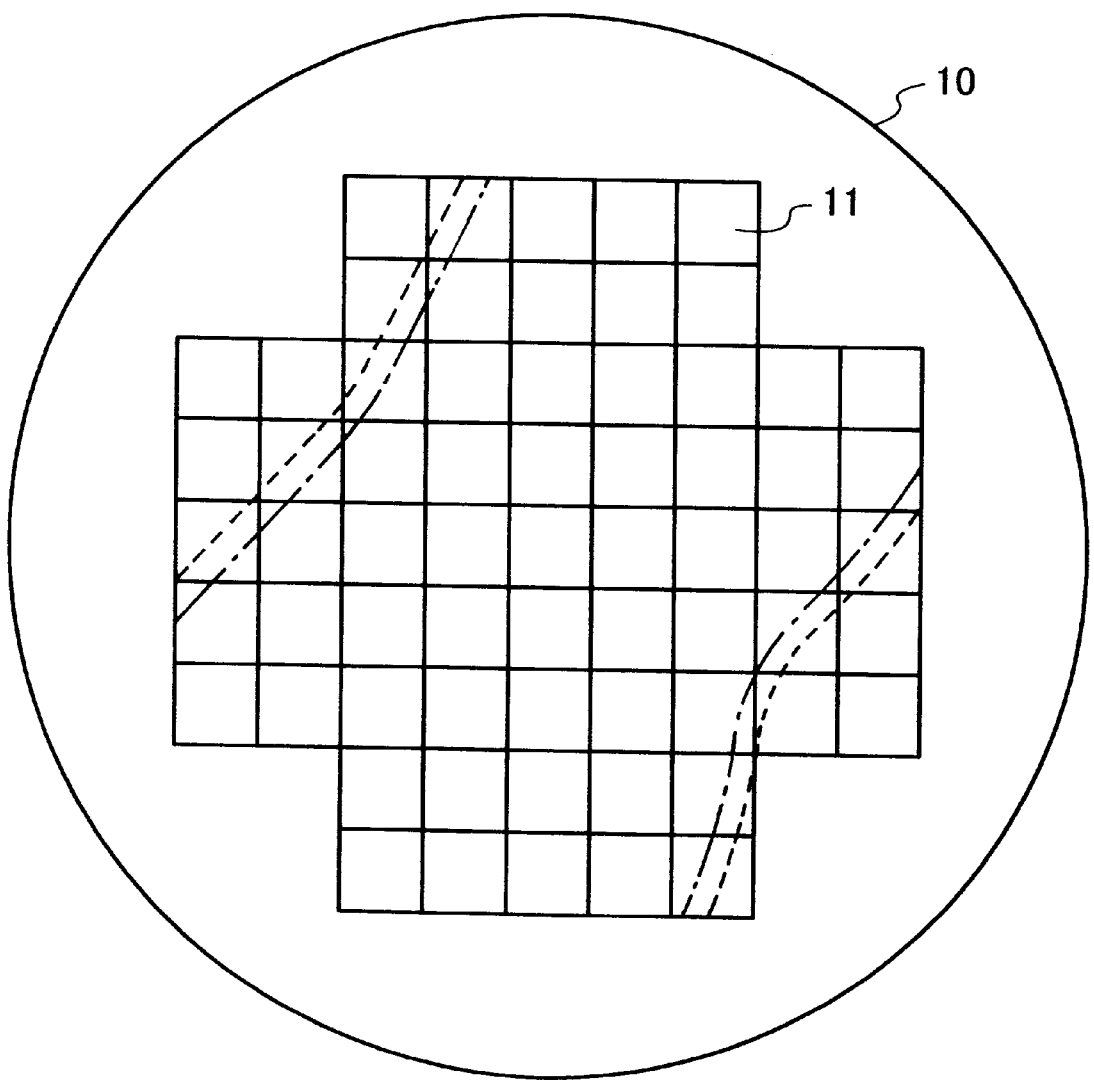
FIG. 15 is an illustration of enlargement of an inspection area in the fifth embodiment according to the present invention.

FIG. 15 is an illustration of the fifth embodiment according to the present invention.

Assume that the dotted lines are the boundary lines of the inspection area determined in the step S5 in FIG. 5. The inspection areas are expanded to a certain extent in the step S5. The alternate long and short dotted lines denote This expansion may be carried out in a case where it is judged in the step S9 in FIG. 5 that the inspection density is necessary.

All the other points of the fifth embodiment are the same as those of the above-described first embodiment.

With the fifth embodiment, it is possible to increase the inspection density easily and effectively.

Sixth Embodiment

FIG. 15 is an illustration of the fifth embodiment according to the present invention.

Assume that the dotted lines are the boundary lines of the inspection area determined in the step S5 in FIG. 5. The inspection areas are expanded in the step S5 in such a way to involve the chip areas in which the boundary line of the inspection area exists. The hatched areas denote the new inspection areas.

This expansion may be carried out in a case where it is judged in the step S9 in FIG. 5 that the inspection density is necessary.

All the other points of the sixth embodiment are the same as those of the above-described first embodiment.

Seventh Embodiment

FIG. 17 is an illustration of the fifth embodiment according to the present invention.

Assume that the dotted lines are the boundary lines of the inspection area determined in the step S5 in FIG. 5. The inspection areas are expanded in the step S5 as shown in FIG. 15 to the boundary of the alternate long and short dotted lines. Further, as shown in FIG. 16, the inspection areas are expanded to the chip areas in which the alternate long and short dotted line exits. Furthermore, in the non-inspection areas, sampling inspection areas such as cross-hatched chip areas are added to improve the reliability of inspection.

This expansion may be carried out in a case where it is judged in the step S9 in FIG. 5 that the inspection density is necessary. Further, in the inspection areas expanded as described above, the bump height may be measured, for example, line by line of bumps, that is, the local inspection density may be made low in order to speed up the inspection than in the other inspection areas. Furthermore, as regards the inspection area before the expansion, the more the deviation of the approximate plane PL from (UL1+LL1)/2 in FIG. 7 becomes, the further the local inspection density may increase.

All the other points of the seventh embodiment are the same as those of the above-described first embodiment.

Eighth Embodiment

Figure 18A:
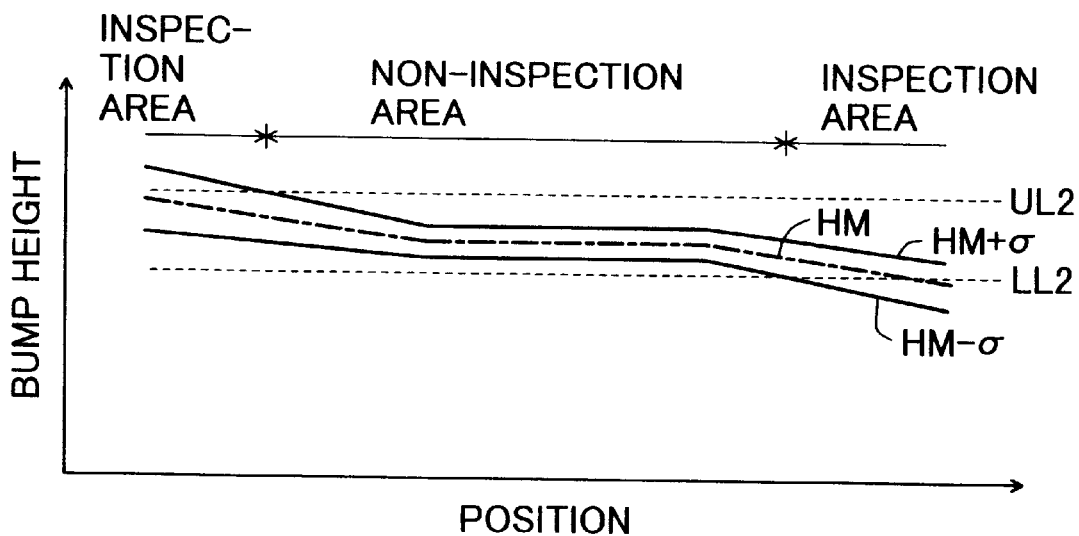
FIG. 18(A) is an illustrative diagram of determining an inspection area in the eighth embodiment according to the present invention.

In the eighth embodiment according to present invention, as shown in FIG. 18(A), as for the respective local areas in the sample area, the respective chip areas for example, the mean height HM and standard deviation $\sigma$ are obtained, and the approximate surfaces of $HM+\sigma$ and $HM-\sigma$ are obtained. If the surface of $(HM+\sigma)$ or $(HM-\sigma)$ is more than the upper limit value UL2 or less than the lower limit value LL2, it is determined as an inspection area.

Figure 18B:
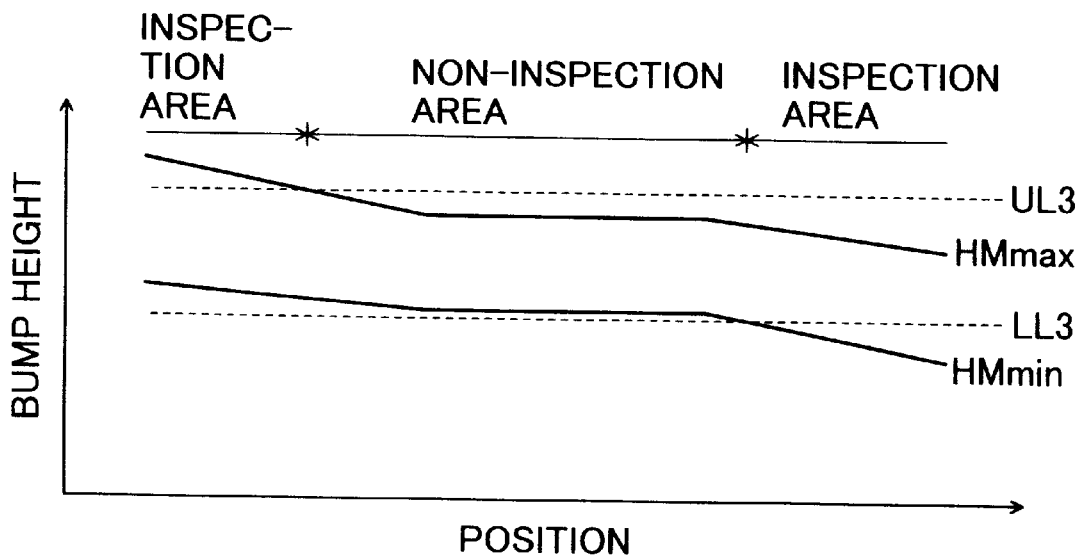
FIG. 18(B) is another illustrative diagram thereof.

FIG. 18(B) shows a modified embodiment for FIG. 18(A). The maximum value HMmax and minimum value HMmin of the bump height for each local area, each chip area for example, in the sample area are obtained, and the approximate surfaces of HMmax and HMmin are obtained as described above. If they are more than the upper limit value UL3 or less than the lower limit value LL3, it is determined as an inspection area.

All the other points of the eighth embodiment are the same as those of the above-described first embodiment.

Ninth Embodiment

Figure 19:
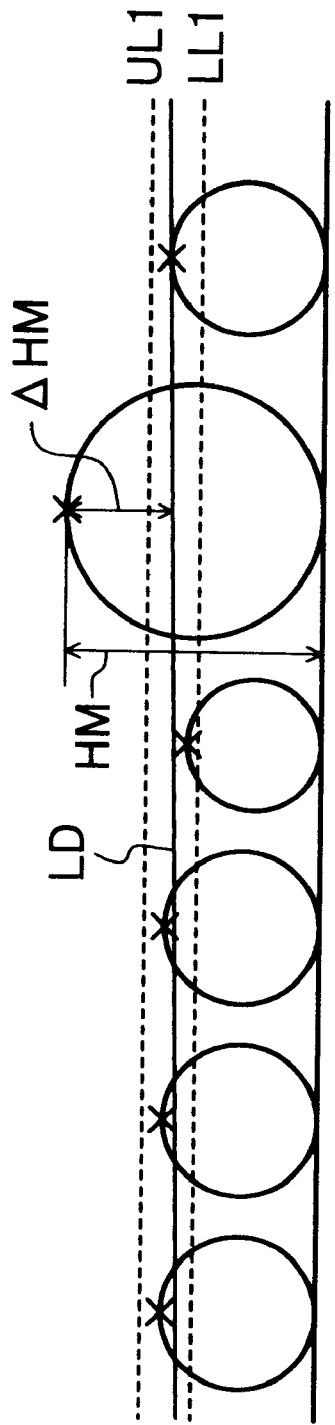
FIG. 19 is a view showing an abnormal value of bump height in a sample area in the ninth embodiment according to the present invention.

FIG. 19 shows an abnormal value of bump height in a sample area in the ninth embodiment according to the present invention.

In a case where a deviation $\Delta HM$ from the approximate line LD of the mean value HM of the bump height in the local areas, chip areas for example, in the sample area exceeds a predetermined value, the inspection area is expanded as described above in the step S5 in FIG. 5, or the inspection density is increased more than in the else case by making the space between the upper limit value UL1 and the lower limit value LL1 narrow, whereby the reliability of inspection will improve.

All the other points of the ninth embodiment are the same as those in the above-described first embodiment.

Tenth Embodiment

Generally, since there is a positive correlation between the height of bumps and the diameter thereof, the diameter of bumps may be measured instead of measuring the height of bumps to use the diameter instead of the height in executing the same processing.

Figure 20A:
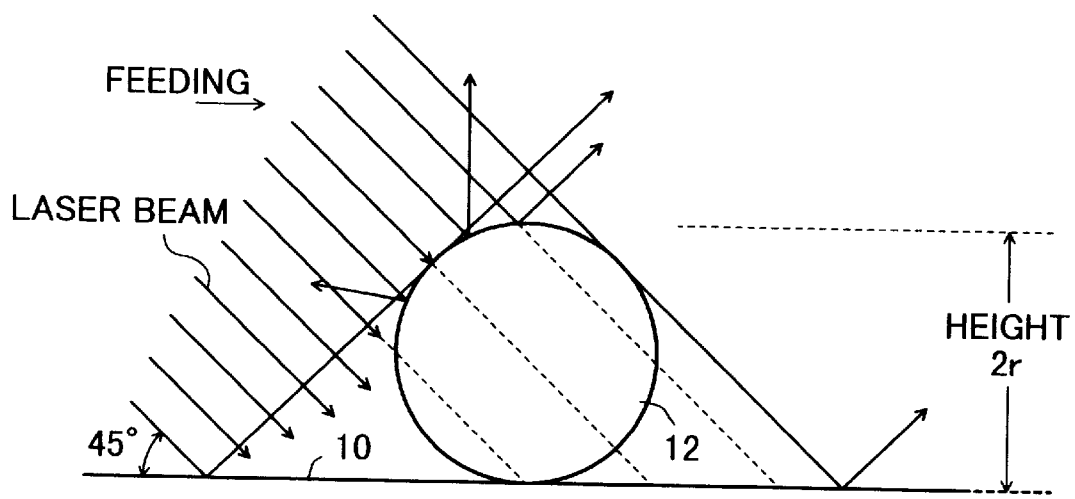
Figure 20B:
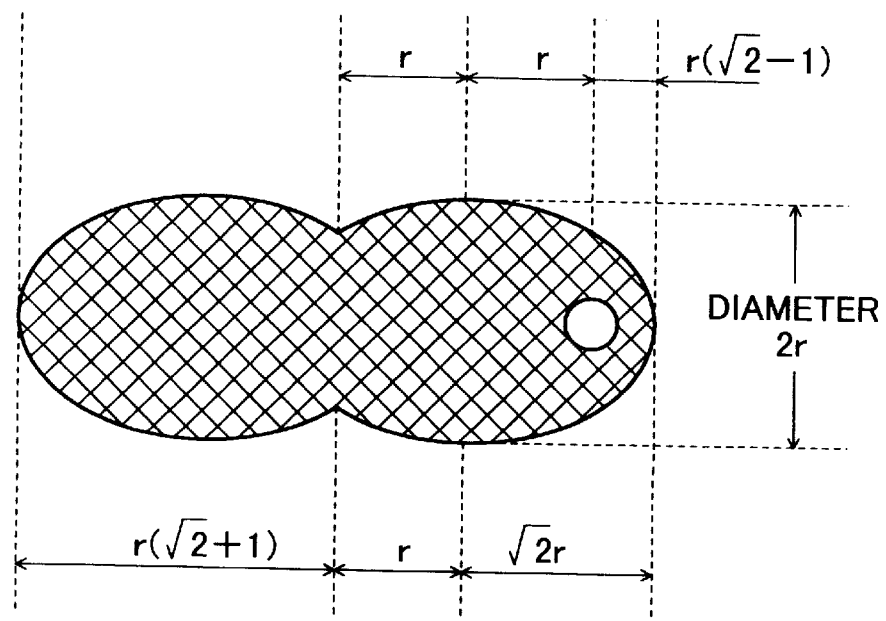

As shown in FIG. 20(A), the bump 12 and its surrounding areas are scanned by the AOD 32 in FIG. 1 with a laser beam in the perpendicular direction to the drawing paper, and feeding by the X-Y-Z stage 20 in FIG. 1 is carried out in the right to left direction in FIG. 20(A), while the brightness B is converted to binary and is written in the memory 59 in FIG. 1, whereby, as shown in FIG. 20(B), a bright and dark image can be obtained. The bump diameter 2r is measured based on the image.

Eleventh Embodiment

Figure 21:
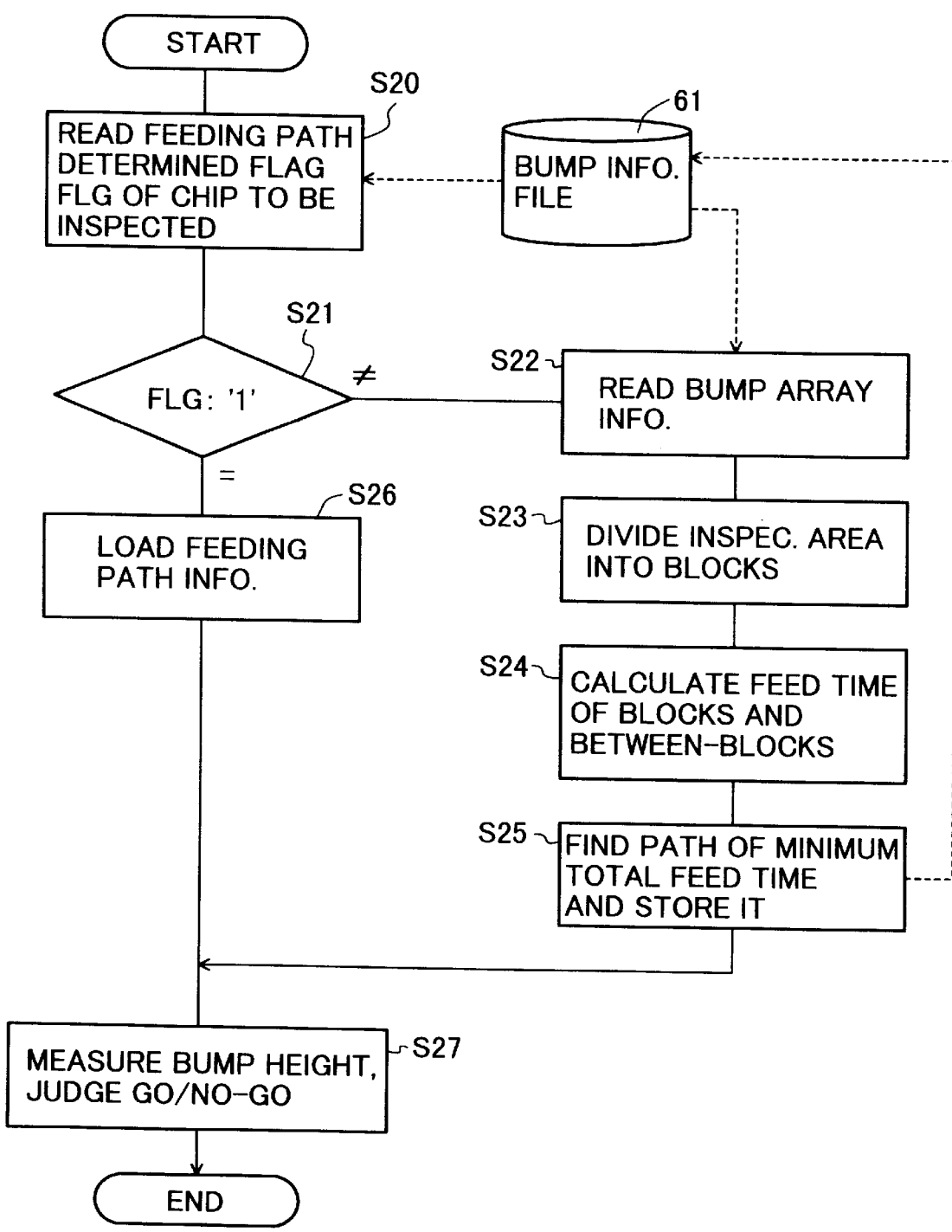
FIG. 21 is a general flowchart showing a procedure of visual inspection in the eleventh embodiment according to the present invention.

FIG. 21 shows a general flowchart showing the visual inspection procedure of the eleventh embodiment according to the present invention.

(S20) A feeding path determined flay FLG corresponding to a chip to be inspected is read from the bump information file 61 in FIG. 1.

Figure 23:
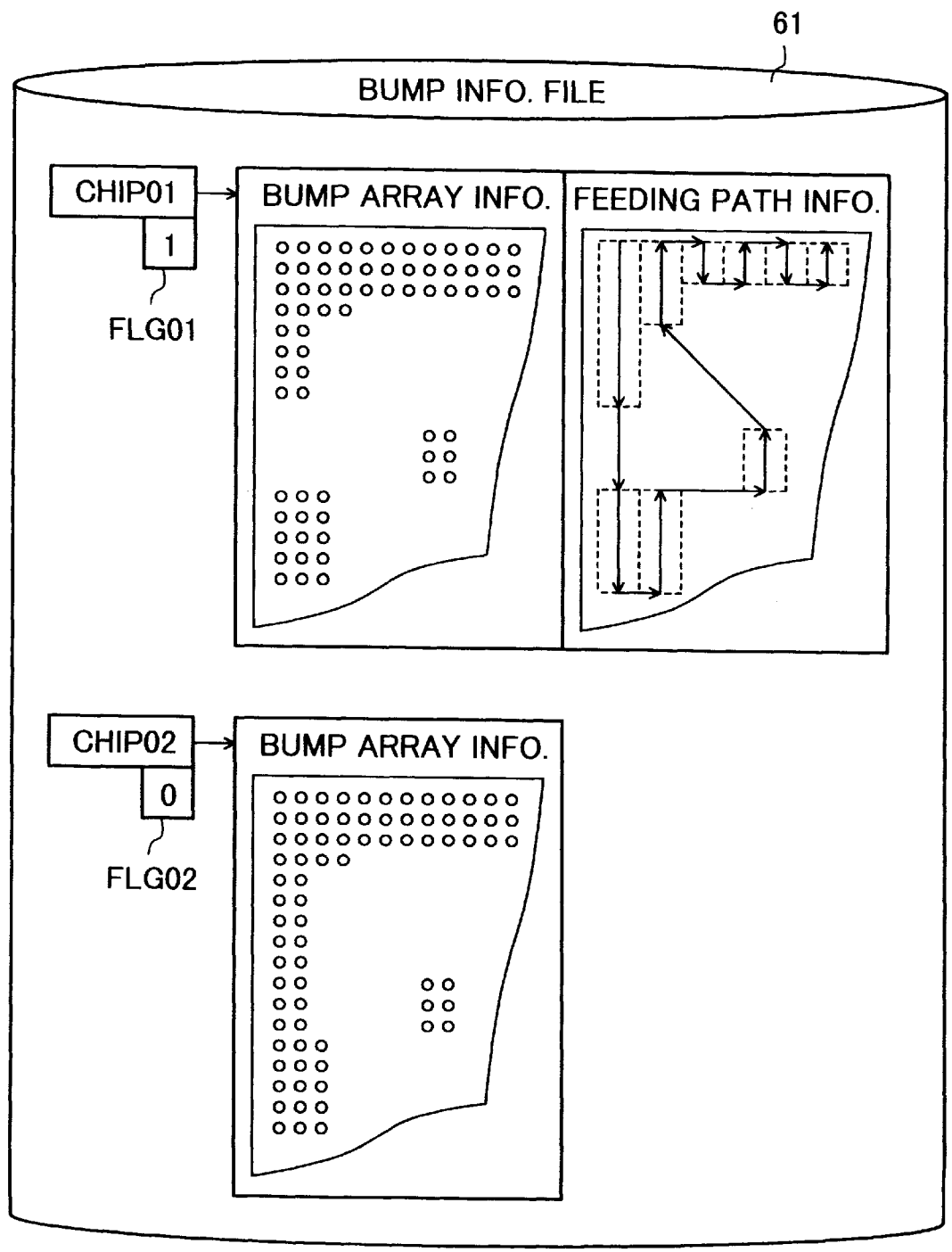
FIG. 23 is an illustration of the contents of a bump information file used in the process of FIG. 21.

As shown in FIG. 23, chip identification codes, CHIP01 and CHIP02, bump array information, information of determined feeding paths of the respective bump arrays, and feeding path determined flags FLG, FLG01 and FLG02, indicating whether or not the corresponding feeding path information exist are related to each other and stored in the bump information file 61. FLG of '1' or '0' denotes whether or not the determined feeding path information exists, respectively.

(S21) If the flag FLG is '0', then the process proceeds to a step S22, or else the process proceeds to a step S26.

(S22) The bump array information corresponding to the chip identification code of the object to be inspected is read from the bump information file 61.

(S23) The inspection area of bumps, for example, all the bump area on a chip is divided into blocks. The division into blocks is to facilitate a determination of a feeding path where feed time is minimized, and a description thereof will be given below.

Referring to FIG. 14, L denotes a feed locus when the X-Y-Z stage 20 is driven with the AOD 32 not operated. X perpendicular to L denotes a scan locus when the AOD 32 is driven. The feeding speed is approximately a predetermined constant value between points P1 and P2 and between points P3 and P4. If the distance between bumps in the feeding direction is more than a predetermined value, such as a distance between points P2 and P3, although the feeding speed may be the same as the predetermined constant value, the feeding is accelerated to speed up the inspection. Therefore, the feeding speed from point P2 to point P3 includes acceleration and deceleration.

Figure 24:
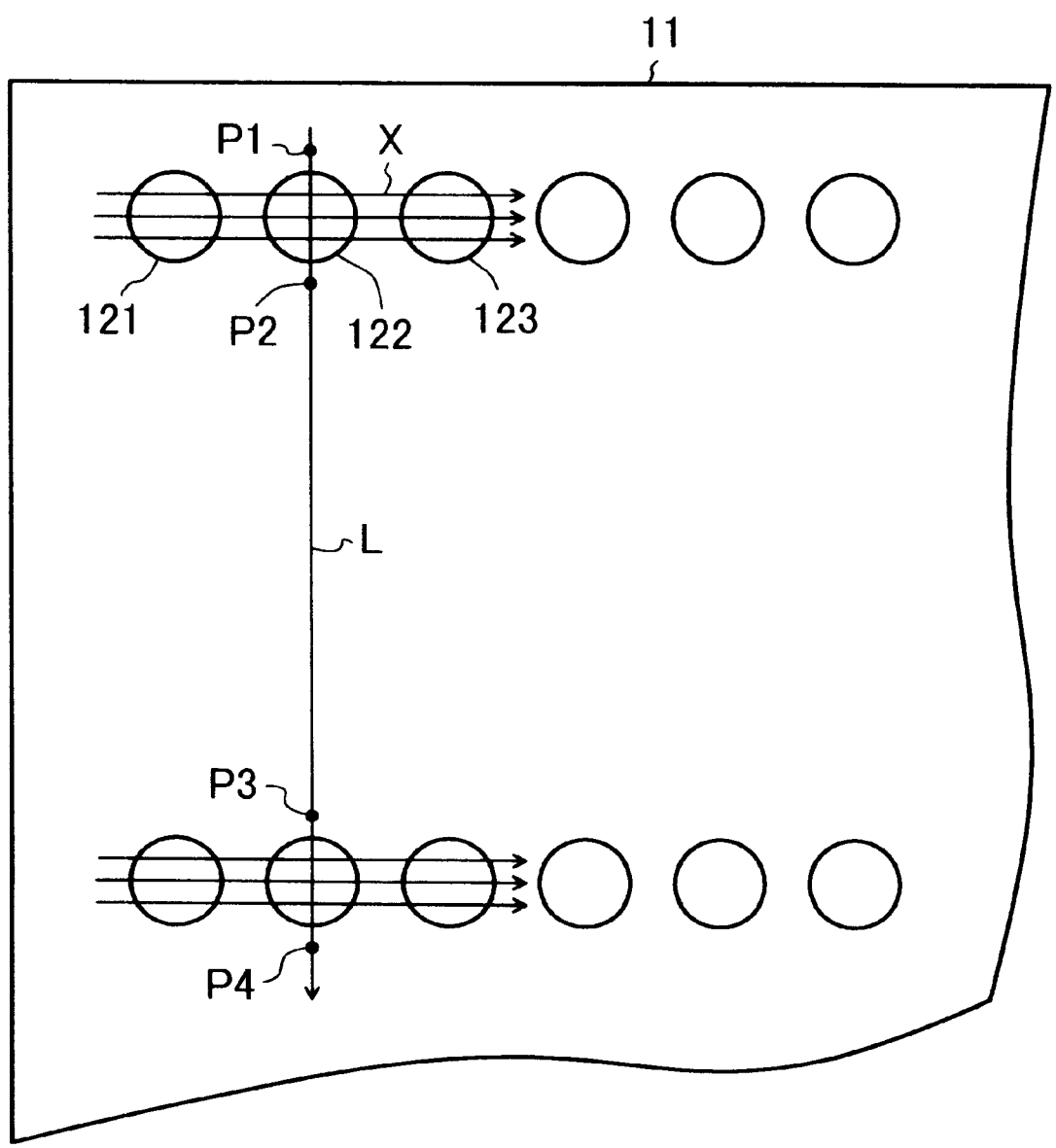
FIG. 24 is an illustration of scanning and feeding for a bump array.

Referring to FIG. 24, rectangles from point P1 to point P2 and from point P3 to point P4, the widths of which are approximately the same as the scanning width, are named as blocks BLK1 and BLK2, respectively. In the same manner, rectangles adjacent to the blocks BLK1 and BLK2 are named as blocks BLK3 and BLK4, respectively. In a case where bumps are arrayed as shown in FIG. 29 in the chip area 11A, the bump array is divided into blocks BLK11 through BLK19 so that, is each block, the distance between bumps in the Y direction becomes less than a predetermined value.

(S24) Block feed time and between-block feed time are calculated.

Figure 29:
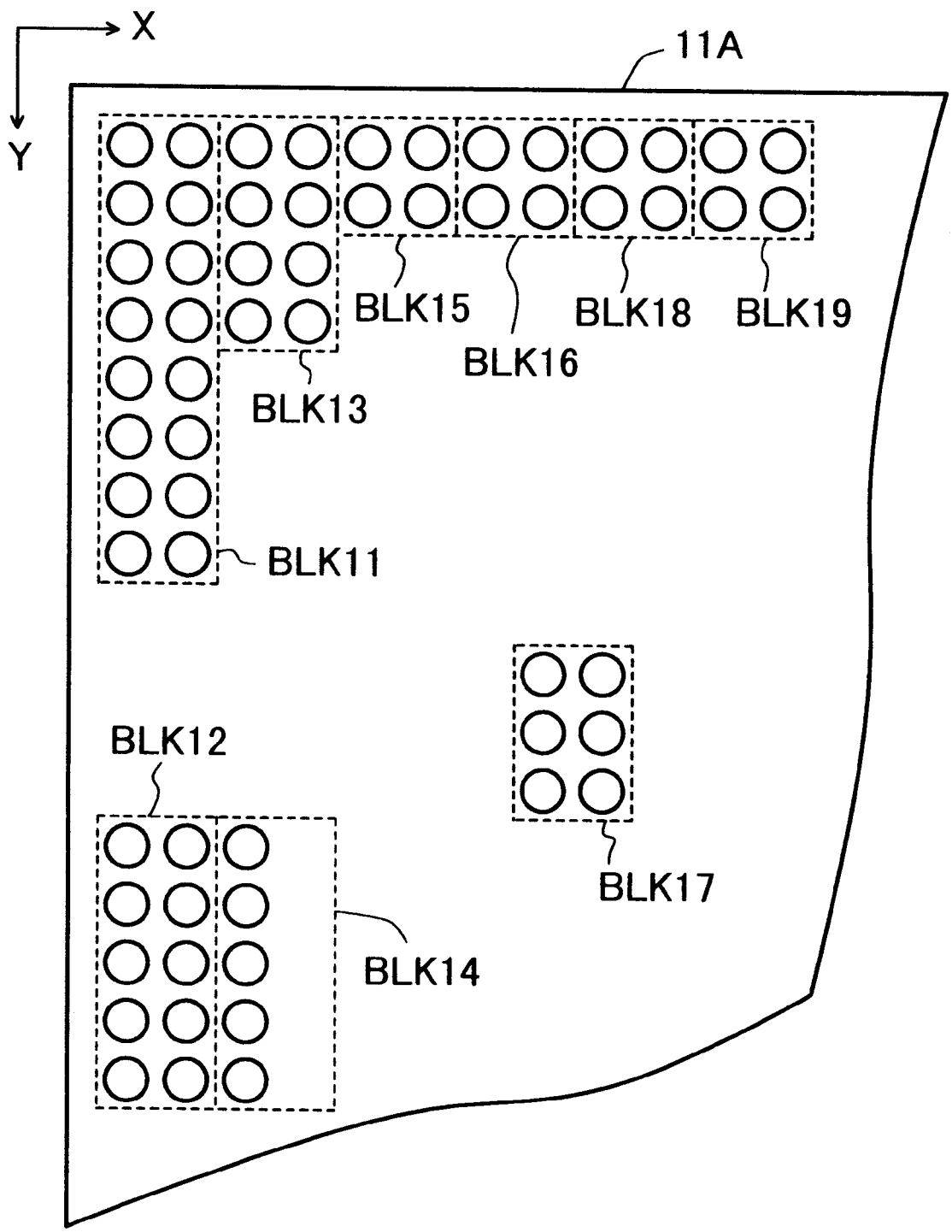
FIG. 29 is an illustration of processing at step S23 in FIG. 21.

Denoting the feed time of a block with a single row as in FIG. 24 as Ta, which value is given in advance, the feed time in blocks, for example, BLK11 and BLK12 in FIG. 29 are 8Ta and 5Ta, respectively.

Figure 25:
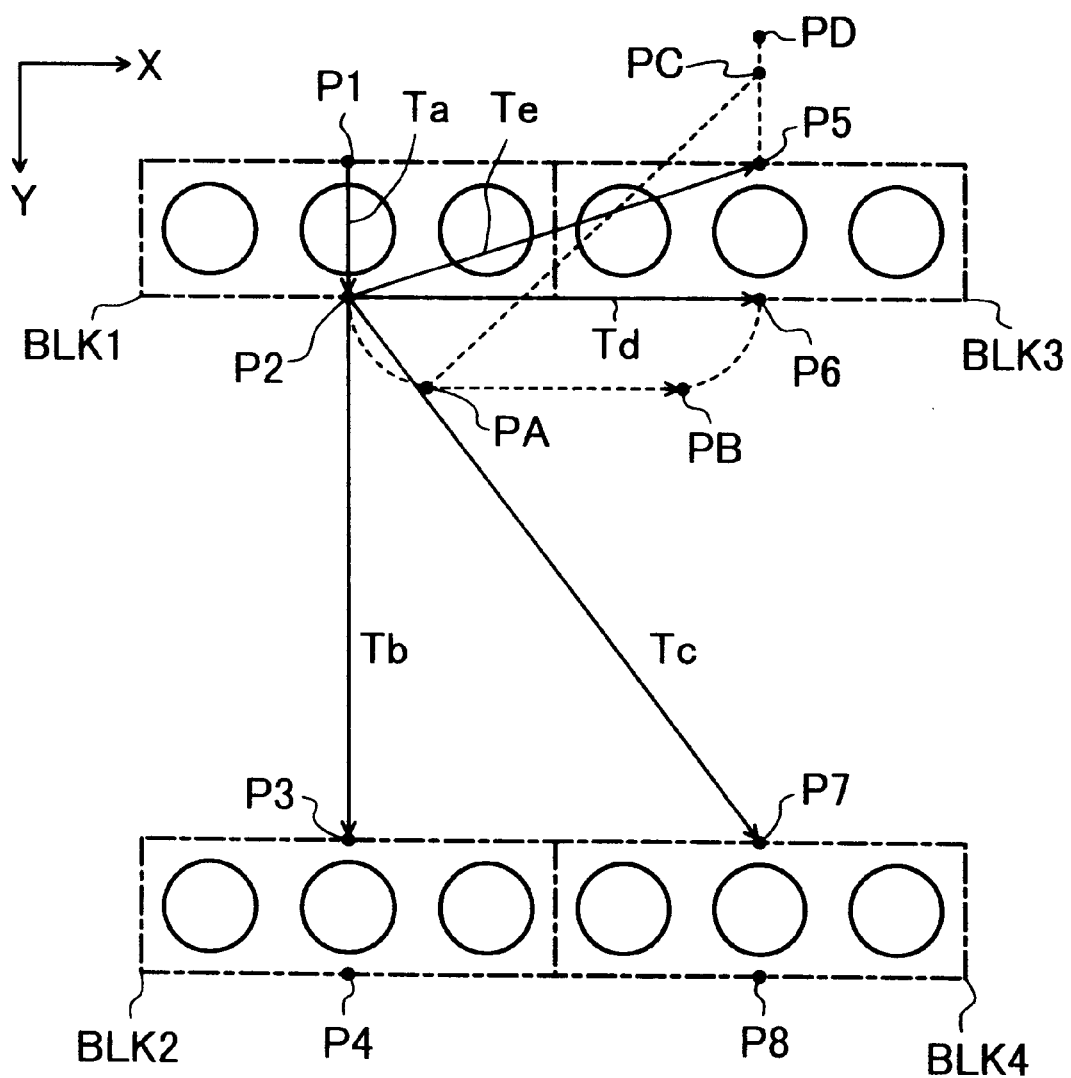
FIG. 25 is an illustration of processing at steps S23 and S24 in FIG. 21.
Figure 26A:
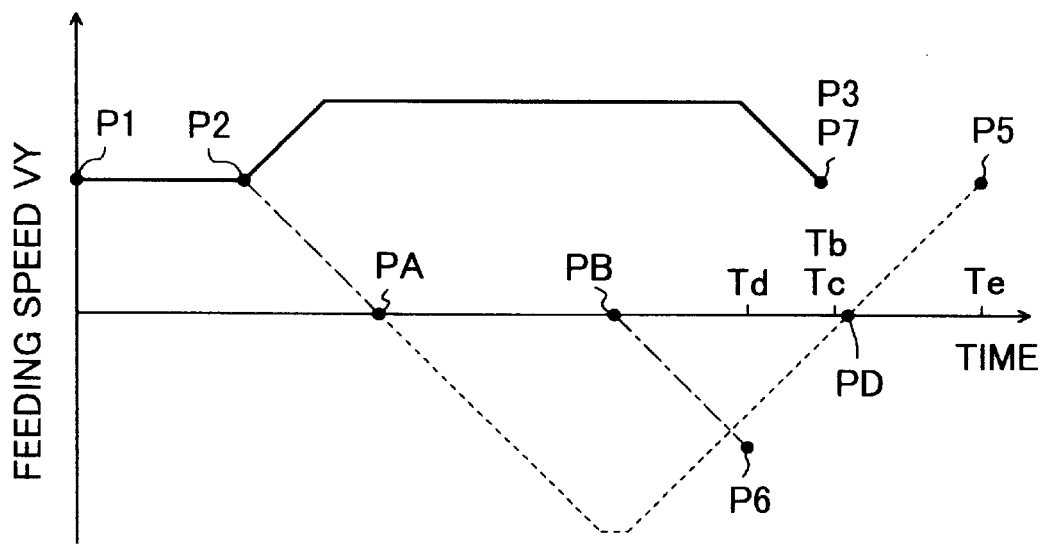
FIG. 26(A) and 26(B) are diagrams showing the feeding speed in the Y and X directions, respectively, along the paths in FIG. 25.
Figure 26B:
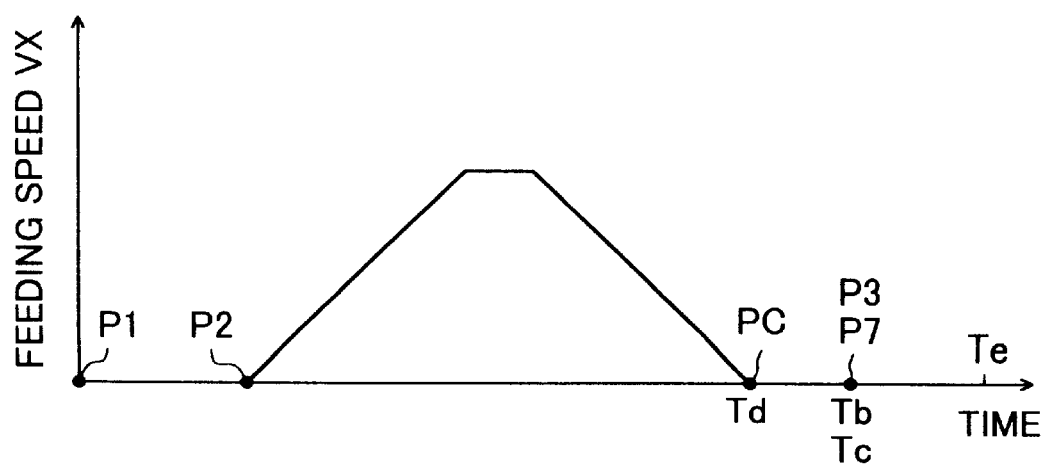

As regards the between-block feed time, in the case of FIG. 25, the feed time Tb from point P2 to point P3, Tc from point P2 to point P7, Td from point P2 to point P6, and Te from point P2 to point P5 are calculated. Solid straight lines having arrows in FIG. 25 denote simplified feed paths, which connect the starting point to the ending points of between-blocks and are not detailed feed paths. Actually, since acceleration and deceleration are included, the exact feed path, for example, from point P2 to point P6 is such as a dotted line, and regarding from point P2 to point PA, the feeding speed VY in the Y direction is decelerated and the feeding speed VX in the X direction is accelerated, regarding from point PB to point P6, the VY is accelerated and the VX is decelerated. The exact feed path from point P2 to point P5 is such as a dotted line which goes from point P2 through points PA, PC, PD and PC to point P5. The feeding speed VX and VY of the paths shown in FIG. 25 are shown in FIG. 26(A) and FIG. 26(B), respectively.

The between-block feed time can be easily calculated by independently calculating the X directional feeding time and the Y directional feed time and selecting a longer time of them, where each thereof is the sum of feed time with accelerated, constant (not zero) and decelerated speed.

The between-block feeding path to be considered is limited to those whose length is within a predetermined range.

(S25) A whole feeding path is formed with connecting between blocks in the inspection area, and the block feed time and between-block feed time, which are calculated in the step S24, in the whole feeding path are added to obtain the total feed time of the path. This process is repeated to find the whole feeding path whose total feed time is minimum.

Figure 27A:
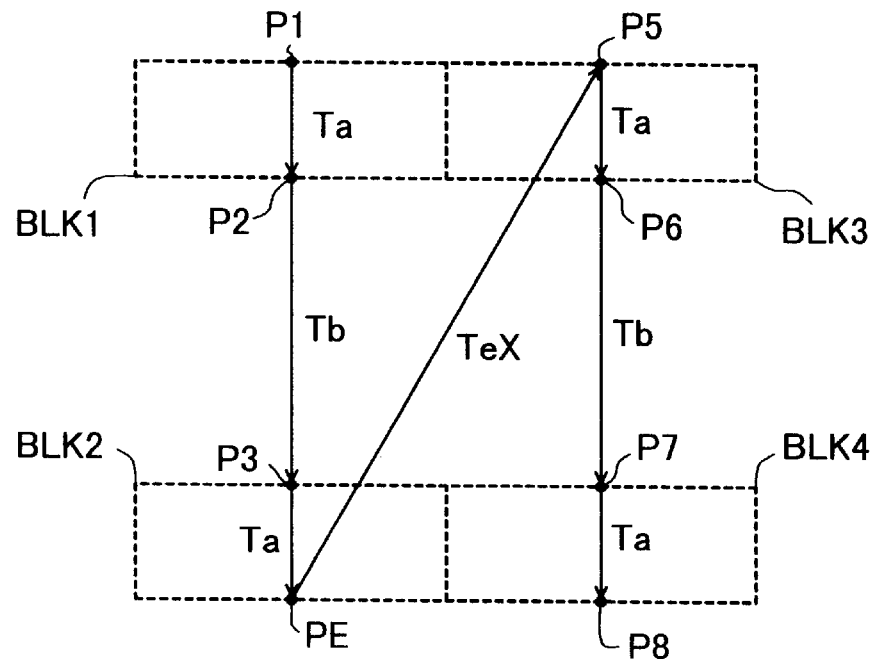
FIG. 27(A) and FIG. 27(B) are illustrations of step S25 in FIG. 21.
Figure 27B:
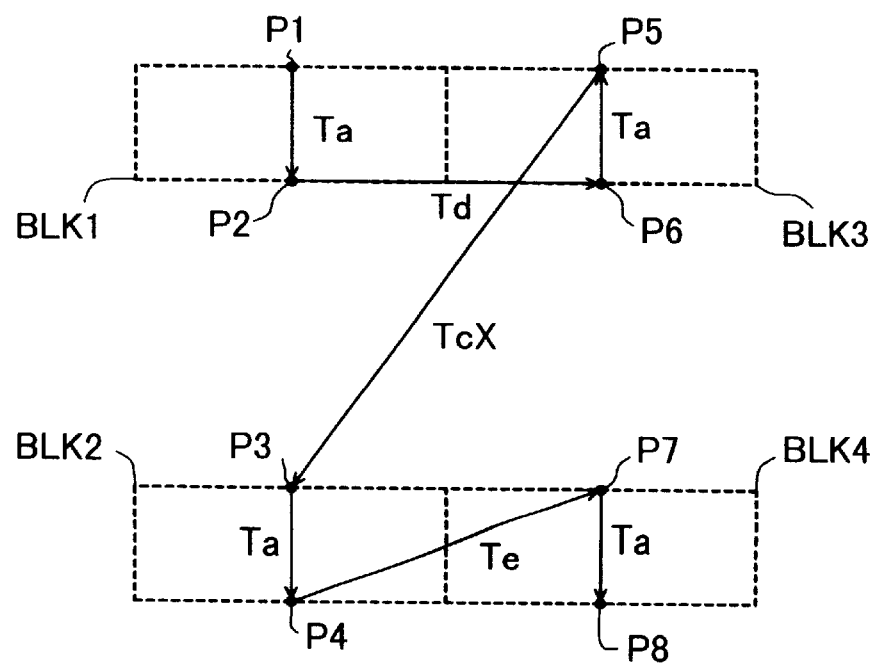

As regards the bump array in FIG. 24 for example, the feed time of such simplified feeding paths as shown in FIGS. 27(A) and 27(B) are calculated. The feed time Tex and Tcx in FIGS. 27(A) and 27(B) are obtained in the same manner as Te and Tc in FIG. 25, respectively.

By separating processes of steps S24 and S25, the same results calculated in the step S24 can be utilized in many paths, resulting in that the total processing time can be shortened.

Figure 22:
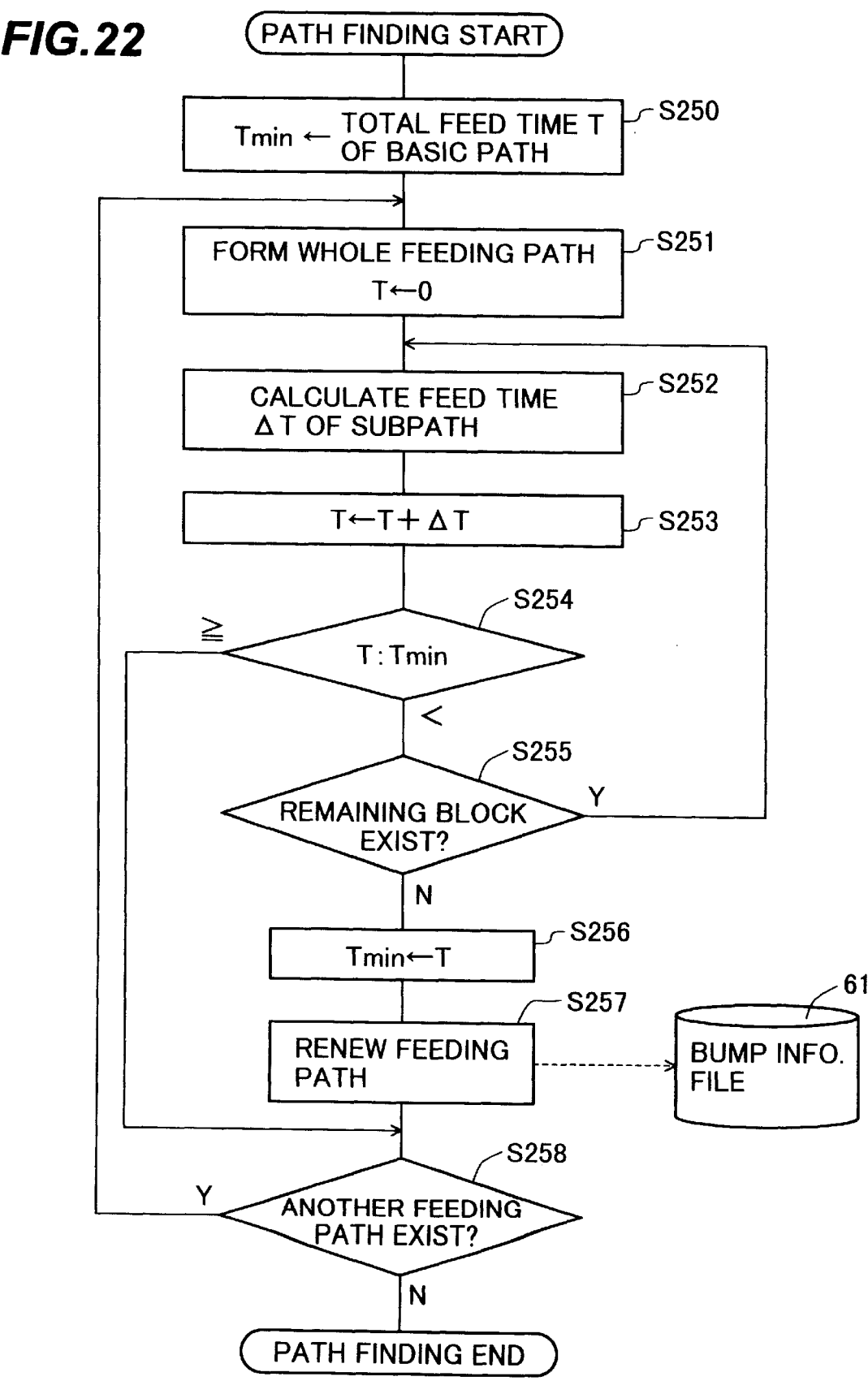
FIG. 22 is a detailed flowchart of step S25 in FIG. 21.

FIG. 22 shows the detail process of the step S25.

Figure 28:
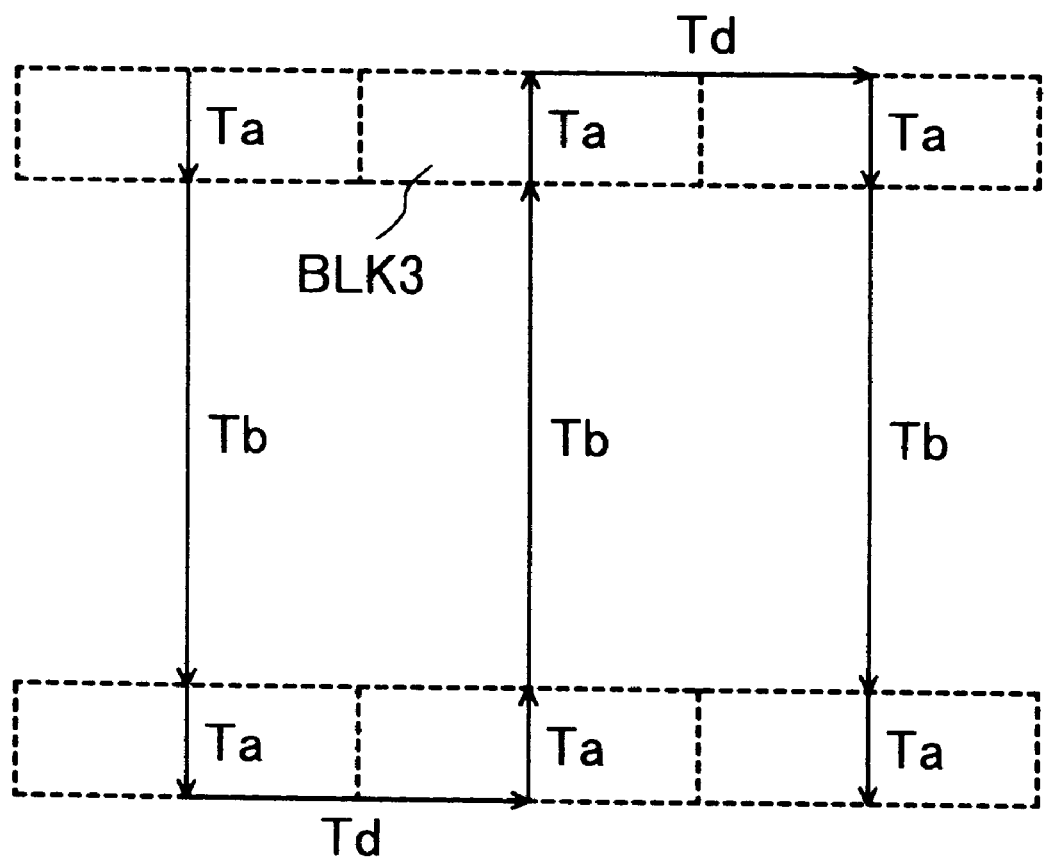
FIG. 28 is an illustration of processing at step S250 in FIG. 22.

(S250) The total feed time T of a basic whole feeding path, for example, a zigzag feeding path as shown in FIG. 28, in the inspection area is calculated, and the total feed time T is substituted as a initial value into a minimum total feed time Tmin.

(S251) A whole feeding path is formed with connecting between blocks in the inspection area. The between-block feeding path to be considered is limited to those whose length is within a predetermined range. The initial value 0 is substituted into the total feed time T.

(S252) The feed time $\Delta T$ of a subpath, for example, a path connecting between ten blocks, is calculated.

(S253) $\Delta T$ is added to T.

(S254) If T>Tmin, then the process proceeds to a step S255, or else the process escapes from the loop of the steps S252 through S255 and proceeds to a step S258 since the feeding path does not have the minimum feed time.

(S255) If there is a remaining block which is not calculated, then the process proceeds to the step S252, or else the process proceeds to a step S256.

(S256) The total feed time T is substituted into the minimum total feed time Tmin.

(S257) To renew, the feeding path having this Tmin is overwritten on the feeding path of the same chip identification code stored in the bump information file 61.

(S258) If there is another candidate of whole feeding path to be considered, then the process returns to step S251, or else the path finding process ends.

Thus, the whole feeding path having a minimum total feed time in the inspection area is stored in the bump information file 61.

Since the time calculation of the remaining feeding path is omitted if $T \geq Tmin$ is judged in the step S254, the processing time is shortened. Further, since, in the step S250, the total feed time of the basic path is calculated, and this is used as a initial value of the minimum total feed time Tmin, it is a higher probability that $T \geq Tmin$ is judged in step S254, than in a case of not using this Tmin. Therefore, the shortening effect is improved.

Next, the process proceeds to step S27.

(S26) The feeding path found in the step S25 is loaded from the bump information file 61, and the process proceeds to step S27.

(S27) Feeding is carried out by the X-Y-Z stage 20 along the above-described found path, the bump height is measured with scanning in the block by the AOD 32 in parallel with the feeding, and if a bump height out of a predetermined range exists in a chip or a chip area, it is judged that the chip or chip area is defective.

In the eleventh embodiment, a feeding path having a minimum feed time is found, and since the feeding is performed along the found feeding path, the feed time is further shortened than before. Further, since a block having a constant feeding speed is considered, and acceleration and deceleration are included in the feeding between blocks, the calculation of the total feed time in an inspection area is simplified, whereby it is possible to easily and speedily find a path having a minimum feed time.

Twelfth Embodiment

In the above-described eleventh embodiment, a description was given of the case where the block feeding direction is only the Y direction. If a case is taken into consideration, where the block feeding direction includes both the X and Y directions, the number of candidates of feeding paths is increased at the step S25 in FIG. 21, and it will be possible to find a feeding path whose feed time is shorter than that of the case of the eleventh embodiment. The block feeding direction may be changed to the X direction, for example, by turning the θ stage 21 in FIG. 1 by 90 degrees.

Figure 30:
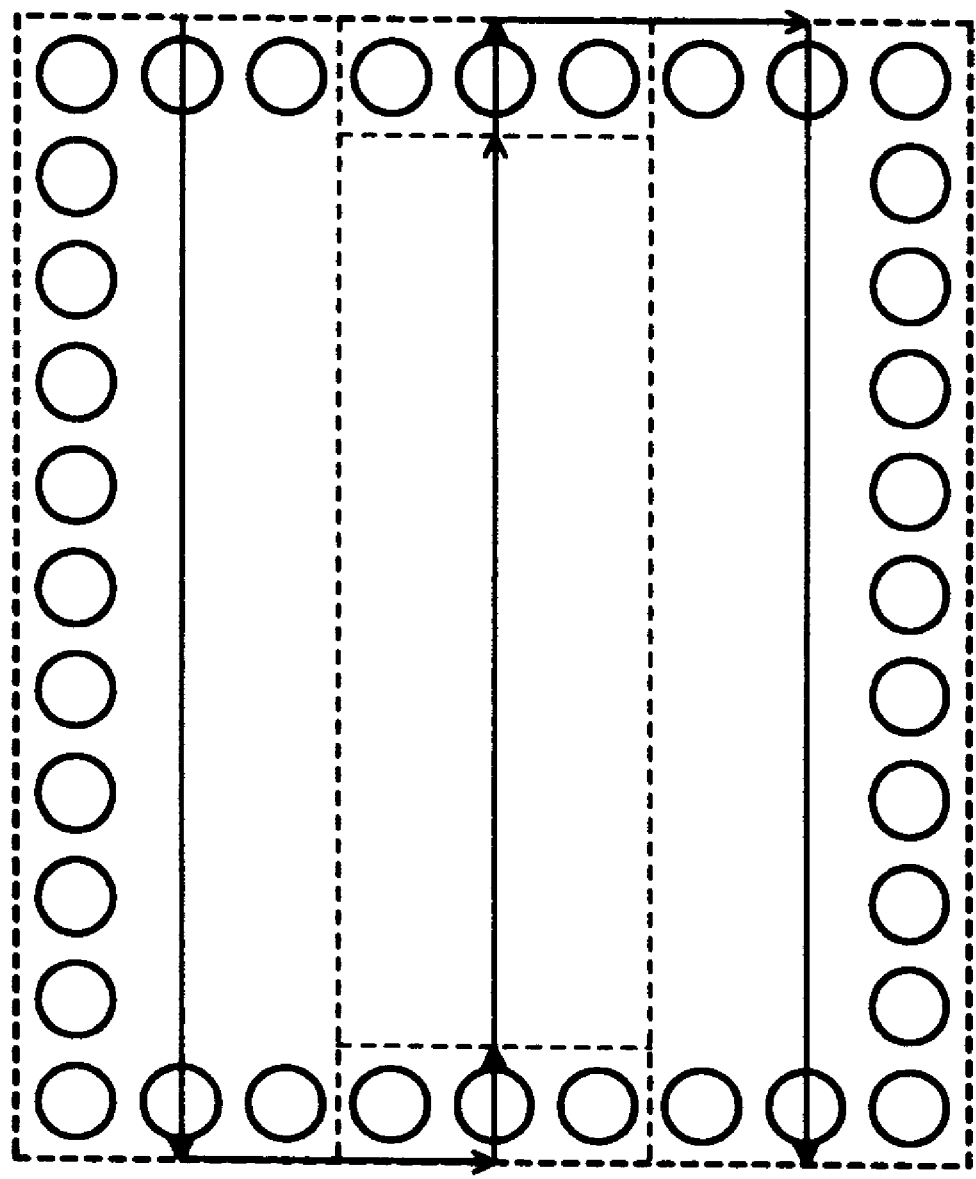
FIG. 30 is a view showing dividing bump array into blocks with one directional feeding and a feeding path.
Figure 31A:
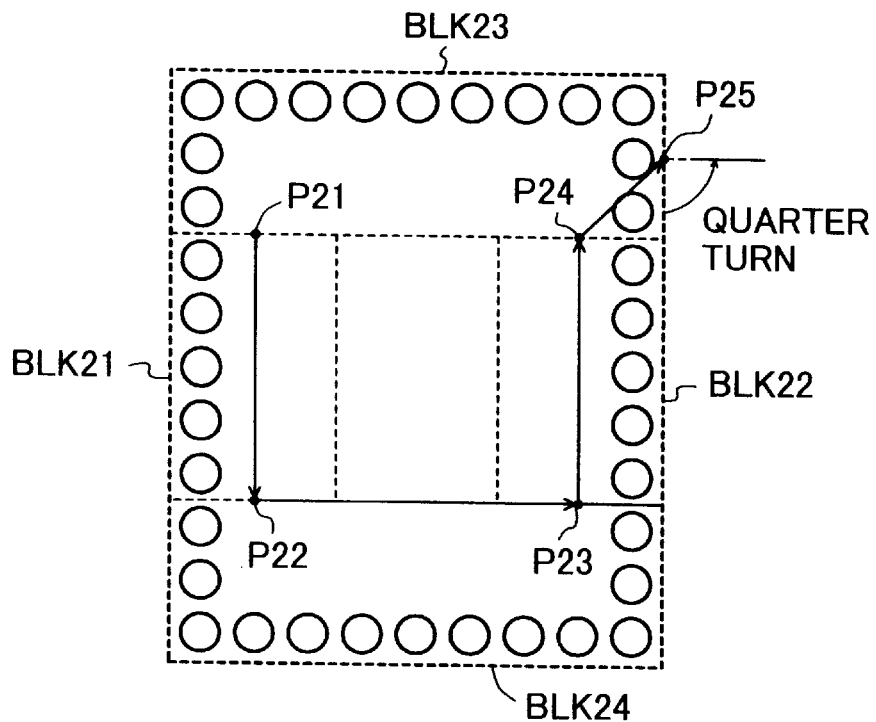
FIG. 31(A) is a view showing dividing the same bump array as that of FIG. 30 into blocks with two directional feeding and a part of feeding path with one direction.
Figure 31B:
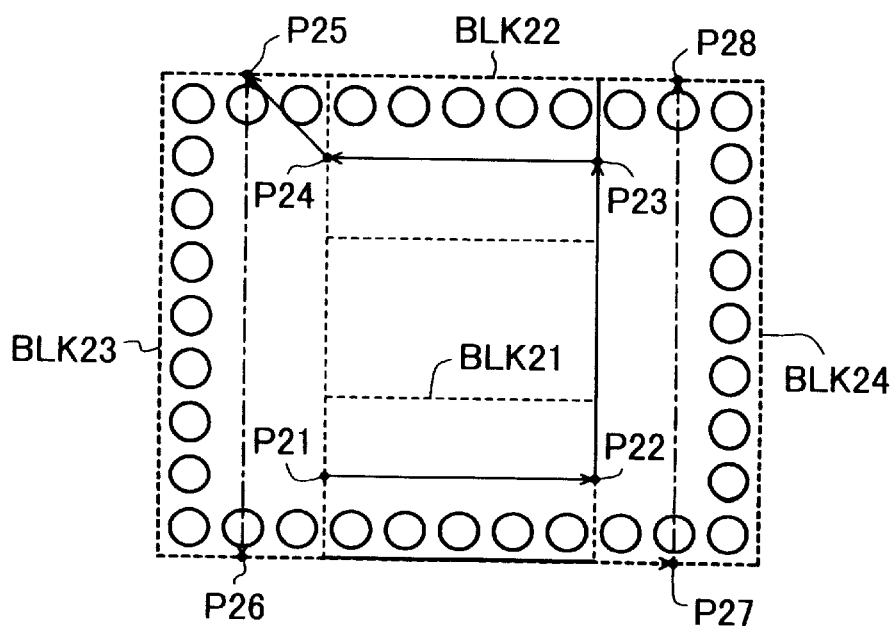
FIG. 31(B) is a view showing the feeding path of FIG. 31(A) and the rest part of the feeding path with one direction after a quarter turn of the bump array.

FIG. 30 shows blocks in a rectangular bump array, in a case where the block feeding direction is only the Y direction, and a zigzag feeding path. While FIGS. 31(A) and 31(B) show a case where the block feeding direction includes both the X and Y directions with respect to the same bump array as FIG. 30. In this example, the bump array is divided into blocks BLK21 through BLK24, and feeding is performed from a point P21 through points P22, P23 and P24 to a point P25. At point P25, by turning the θ stage 21 in FIG. 1 in the arrow direction around this point by 90 degrees, the bump array becomes as shown in FIG 31(B), and then the feeding is performed from the point P25 through points P26 and P27 to a point P28.

The tool feed time also includes the turning time of the θ stage 21. If the θ stage 21 is turned during feeding between blocks by the X-Y-Z stage 20, the total feed time will be shortened.

Figure 32:
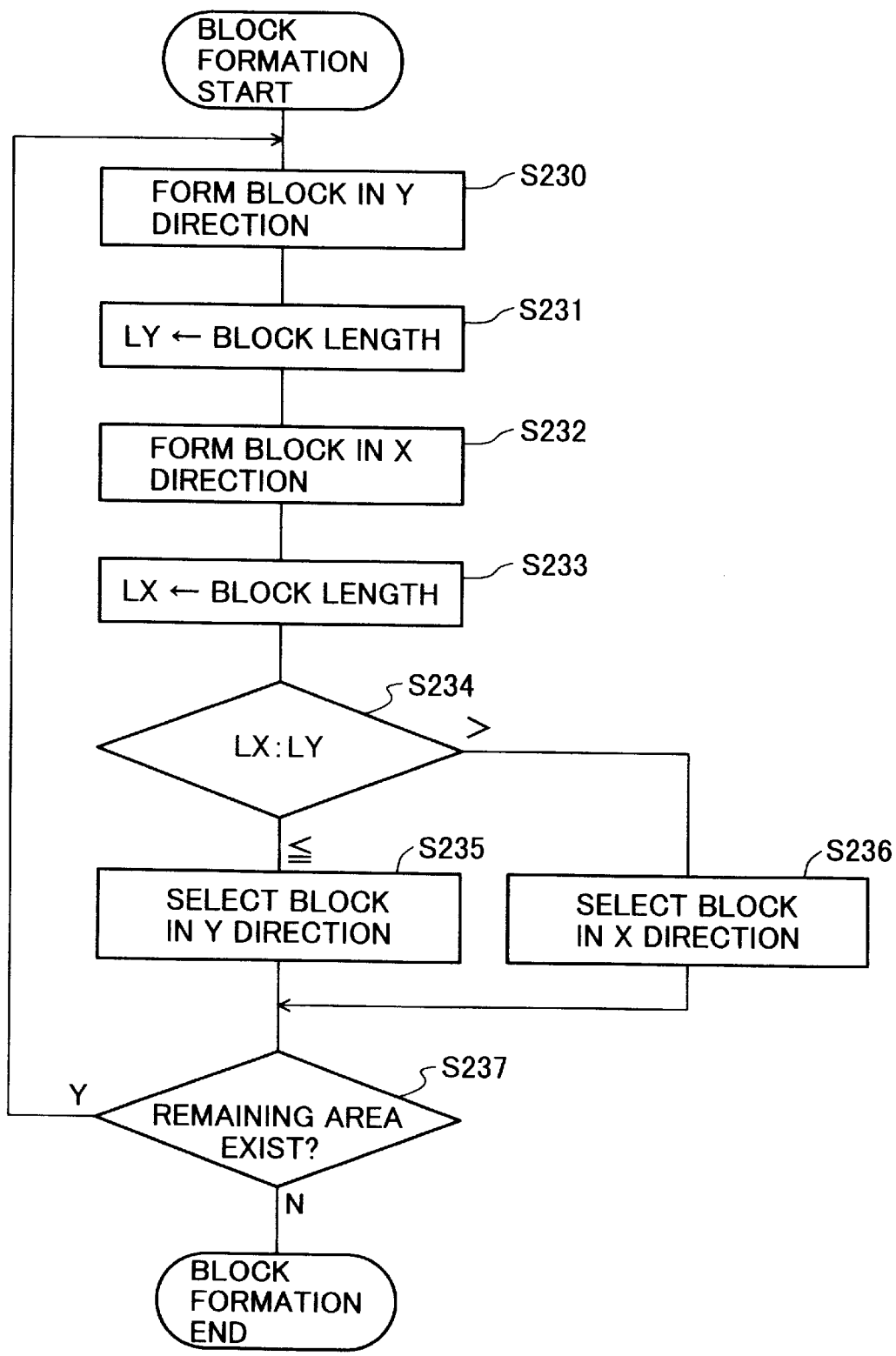
FIG. 32 is a flowchart showing an algorism of dividing bump array into blocks with two directional feeding, of the twelfth embodiment according to the present invention.

FIG. 32 shows an algorism of dividing into blocks with feeding of both the X and Y directions. The process of FIG. 32 is carried out at the step S23 in FIG. 21.

(S230) From the side where the X value is smaller, one block in the Y direction is formed as a block candidate. The length of the block in the Y direction is determined by a limitation in that the distance between adjacent bumps in the Y direction in the same block must be less than a predetermined value, as in the case of the above-described eleventh embodiment. The width of the block in the X direction is approximately the same as the scanning width.

Figure 33:
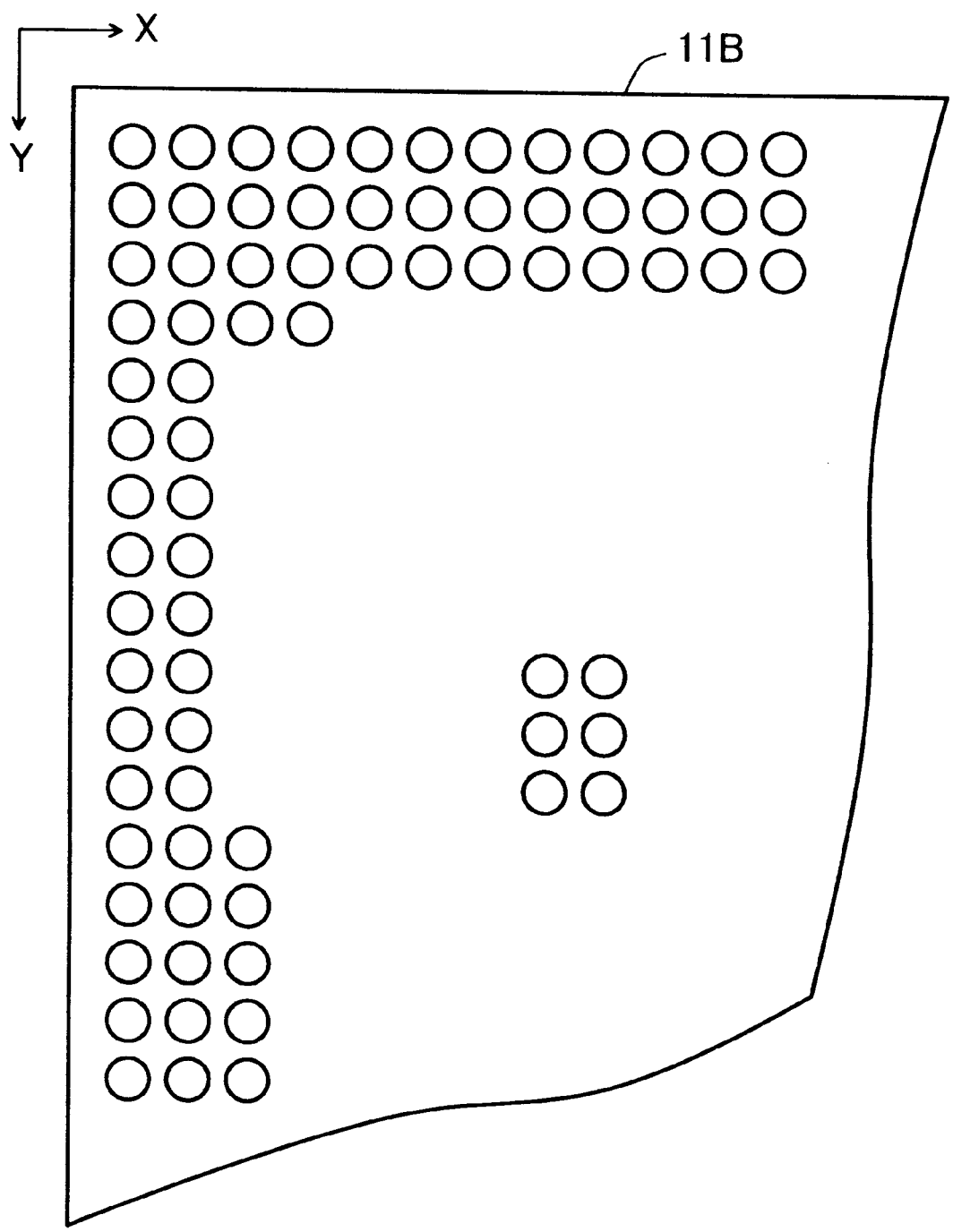
FIG. 33 is a view showing an example of a bump array to which the process of FIG. 32 is applied.
Figure 37A:
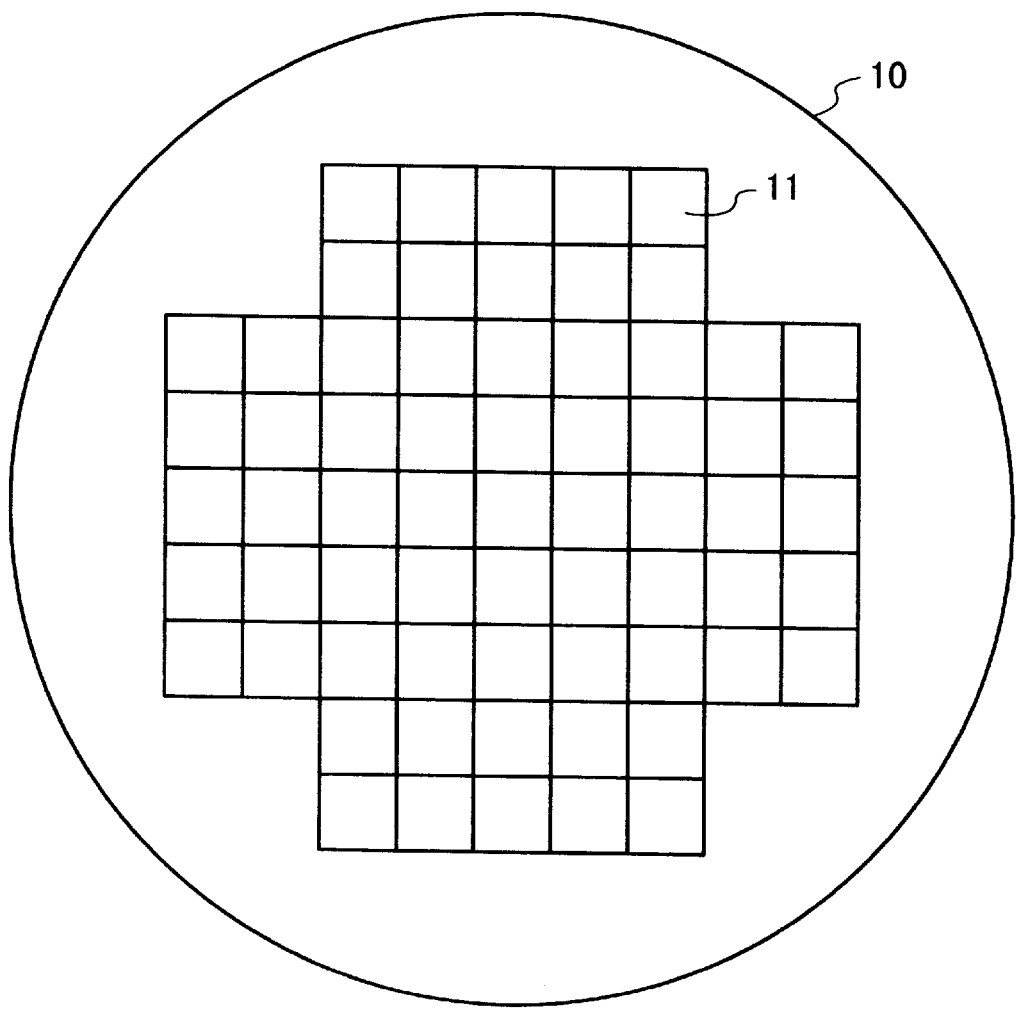
FIG. 37(A) is a plan view of a wafer on which chip areas are formed.
Figure 37B:
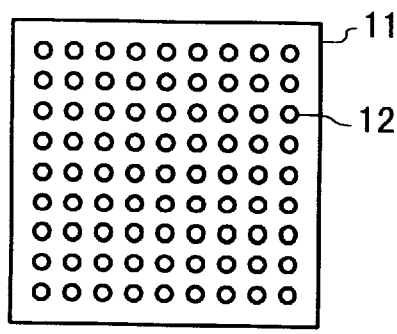
FIG. 37(B) is a bump array view on a chip area.

For example, as regards a chip area 11B of such a bump array as shown in FIG. 33, a block BLK32Y shown in FIG. 34(A) is formed.

(S231) The length of this block is substituted into LY.

(S232) In the like manner as the step S230, from the side where the Y value is smaller, another block in the X direction is formed as another block candidate. The length of the block in the X direction is determined by a limitation in that the distance between adjacent bumps in the X direction in the same block must be less than the predetermined value. The width of the block in the Y direction is approximately the same as the scanning width.

(S233) The length of this block is substituted into LX.

(S234 through S236) If LX≦LY, then the block candidate formed in step 230 is selected, or else the block candidate formed in step S232 is selected.

In the case of FIG. 34(A), the block BLK31Y is selected, and the block BLK31X is cancelled.

(S237) If there remains a bump which is not in a block, then the process returns to step S230, or else the block making process ends.

In the second loop of the steps S230 through S237, in FIG. 34(B), candidates of blocks BLK32Y and BLK32X are formed and the block BLK32X is selected. In the third loop, in FIG. 35(A), candidates of blocks BLK33Y and BLK33X are formed and the block BLK33X is selected. In the fourth loop, in FIG. 35(B), candidates of blocks BLK34Y and BLK34X are formed and the block BLK34Y is selected. In the fifth loop, in FIG. 36(A), candidates of blocks BLK35Y and BLK35X are formed and the block BLK35Y is selected.

By such a process for the bump array of FIG. 33, such blocks as shown in FIG. 36(B) are easily obtained as a result.

Although preferred embodiments of the present invention has been described, it is to be understood that the invention is not limited thereto and that various changes and modifications may be made without departing from the spirit and scope of the invention.

For example, both the height and diameter of bumps may be measured, the volume of the bump may be approximated to a value which is proportional to the produce of the square of the diameter and the height, and with using the volume instead of the above-described height, a process which is similar to the above description may be carried out. Further, the volume of the bump may be approximated to a value which is proportional to the cube of the height or diameter of the bump.

Objects to be inspected are not limited to wafers on which flip chips are formed, and they may be individual flip chips cut and separated from a wafer.

Further, two sets of the light beam scanner 30 and height detector 40 may be provided, not using the θ stage 21, one set thereof may be used to perform scanning in the X direction while the other set thereof may be used to perform feeding in the Y direction, whereby light beam scanning may be changed from the X direction to the Y direction or vise verse at a high speed.

Such a construction may be employed that the axis of the light beam scanner 30 is disposed perpendicular to a wafer 10 and the axis of the height detector 40 is dispose in a diagonal direction. In this case, if the AOD 32 which is enough that one set of the light beam scanner 30 and the height detector 40 is provided without using the θ stage 21.

A two-dimensional image sensor may be used instead of the PSD 43. In this case, such a construction may be employed that line-shaped light is irradiated onto a chip with employing a cylindrical lens or a flat bundle of optical fibers in a light beam scanner. As another construction similar to that the two-dimensional sensor is used, a one-dimensional sensor and galvanomirror may be employed instead of the two-dimensional sensor.

Further, with converting the brightness B into binary data and writing the data into the memory 59 to get binary image of the bumps instead of measuring the height of bumps, the bump diameter may be measured from the binary image of the bumps.

If either the height or diameter of a bump is out of a predetermined range after measuring both height and diameter of the bump, it may be judged to be defective.

Furthermore, if a bump array to be inspected is symmetrical, a feeding path of a minimum feed time may be found in regard to only one part of a symmetrical pair thereof.

The process of the steps S22 through S25 in FIG. 21 may be carried out with another computer which is different from the processing unit 55 in FIG. 1.

What is claimed is:

1. A method of visually inspecting bumps arrayed on a substrate with measuring a geometrical quantity of said bumps, comprising the steps of:

determining a sample area having part of said bumps;

measuring said geometrical quantity of said bumps in said sample area;

estimating a geometrical quantity distribution of said bumps on said substrate based on the measured value at the step;

determining an inspection area based on said geometrical quantity distribution; and measuring said geometrical quantity of said bumps in said inspection area instead of all said bumps on said substrate.

2. A method according to claim 1, wherein said substrate is a semiconductor wafer on which chip areas are arrayed, and said method further comprises the step of, after the step, judging that a chip area, in which there is a bump of said measured value being out of a predetermined range, is defective.

3. A method according to claim 1, wherein said geometrical quantity includes either height, diameter or volume of said bumps.

4. A method according to claim 1, wherein the step, the whole bump area on said substrate is divided into a plurality of sub areas before said estimating, and said estimating is performed in regard to each of said sub areas.

5. A method according to claim 1,
wherein, in the step, said geometrical quantity distribution is expressed in terms of an surface on which estimated values of the measured geometrical quantity exist, and
wherein, in the step, said inspection area is determined on the basis that whether the height of said surface is in a predetermined range or not.

6. A method according to claim 1, wherein said step comprises the steps of:
obtaining means values and standard deviations of the measured geometrical quantity of respective local areas in said sample area; and
estimating distributions of mean heights and standard deviations of respective local areas in the whole area on said substrate, and
wherein, in said step, said inspection area is determined on the basis of the estimated distributions.

7. A method according to claim 1, wherein said step comprises the steps of:
obtaining maximum and minimum values of the measured geometrical quantity of respective local areas in said sample area; and
estimating distributions of maximum and minimum values of respective local areas in the whole area on said substrate, and
wherein, in said step, said inspection area is determined on the basis of the estimated distributions.

8. A method according to claim 1, wherein, in said step, inspection density is increased when a deviation exceeding a predetermined value is included in the measure values in the step.

9. A method according to claim 1, further comprising the step of accumulating data of said inspection areas and inspection results,
wherein, in said step, inspection density is determined on the basis of the accumulated data.

10. A method according to claim 9,
wherein, in said step, said data are classified according to formation conditions of said bumps, and
wherein, in said step, said inspection density is determined on the basis of corresponding one of said classified data of the accumulated data.

11. A method according to claim 10, wherein said formation conditions of said bumps are plating baths in which plating of said bumps are performed.

12. A method according to claim 8, wherein, in said step, said inspection density is increased with widening said inspection area.

13. A method according to claim 12, wherein, in said step, said inspection density is increased with including a chip area having a boundary of said inspection area.

14. A method according to claim 12,
wherein, in the step, said geometrical quantity distribution is expressed in terms of an surface on which estimated values of the measured geometrical quantity exist, and
wherein, in the step, said inspection area is determined on the basis that whether the height of said surface is in a predetermined range or not, and said inspection density is increased with changing this predetermined range.

15. A method according to claim 12, wherein, in the step, said inspection density is increased with adding a random sampling inspection area.

16. An apparatus for visual inspection of bumps arrayed on a substrate, comprising:
a measuring device for measuring a geometrical quantity of bumps;
a storage device for storing array data of said bumps on said substrate; and
a processor for:
causing said measuring device to measure said geometrical quantity of bumps in a sample area on said substrate with reference to said data;
estimating a geometrical quantity distribution of said bumps on said substrate based on the measured value of said geometrical quantity;
determining an inspection area based on said geometrical quantity distribution; and
causing said measuring device to measure said geometrical quantity of said bumps in said inspection area instead of all said bumps on said substrate.

17. A method visually inspecting bumps arrayed on a substrate with measuring a geometrical quantity of said bumps, comprising the steps of:
dividing an inspection area into rectangular blocks with width thereof being approximately equal to a light beam scanning width and feeding path being a direction perpendicular to said width;
finding a whole feeding path in said inspection area, whose total feed time of block feed time and between-block feed time is minimum, from a plurality of whole feeding paths; and
measuring said geometrical quantity with feeding said substrate along the found whole feeding path, scanning light beam for said bumps and receiving reflected light.

18. A method according to claim 17, wherein, in the step, said block feed time and said between-block feed time are calculated on the condition that block feeding speed is constant and acceleration and deceleration are involved in between-block feeding.

19. A method according to claim 17, wherein, in the step, said total feed time is calculated with accumulating feed time of sub feeding path, and when the accumulated feed time becomes greater than the so-far-minimum value of the total feed time, the calculation of the remaining feed time is omitted.

20. A method according to claim 19, wherein, in the step, the total feed time of a predetermined whole feeding path is firstly calculated in order to get an initial value of said so-far-minimum value.

21. A method according to claim 17, wherein, in the step, each of said rectangular blocks is determined so that any adjacent bump interval therein in the feeding path direction is less than a predetermined value.

22. A method according to claim 21, wherein the step comprises the steps of:

forming two rectangular block candidates in first and second feeding path directions, respectively, in such a way that said first and second feeding path directions are perpendicular to each other and one end portions of said two rectangular block candidates overlap; and selecting one, with longer feeding path, of said two rectangular block candidates;

wherein the steps and are repeatedly performed until any bump in said inspection area is within a block.

23. A method according to claim 22, wherein, in the step, said substrate is turned by 90 degrees after scanning a block of said first feeding path direction and before scanning a block of said second feeding path direction.

24. An apparatus for visual inspection of bumps arrayed on a substrate, comprising:

a storage device for storing array data of said bumps on said substrate; and a stage for feeding said substrate mounted thereon;

measuring device, for measuring a geometrical quantity of bumps, with irradiating a light beam onto bumps, scanning said light beam and receiving reflected light;

a processor for:

with reference to said array data, dividing an inspection area into rectangular blocks with width thereof being approximately equal to a light beam scanning width and feeding path being a direction perpendicular to said width;

finding a whole feeding path in said inspection area, whose total feed time of block feed time and between-block feed time is minimum, from a plurality of whole feeding paths; and causing said stage to feed said substrate along the found whole feeding path.

25. An apparatus according to claim 24, wherein said measuring device comprises:

a light beam scanning device for irradiating said light beam onto bumps and scanning said light beam; and a geometrical quantity detecting device for detecting said geometrical quantity with receiving light reflected from a bump.

* * * * *